(12) United States Patent
Wong et al.

(10) Patent No.: US 10,640,806 B2
(45) Date of Patent: *May 5, 2020

(54) RESTORING FUNCTION OF TUMOUR ACIDIFIED T CELLS

(71) Applicant: Helix BioPharma Corp., Richmond Hill (CA)

(72) Inventors: Wah Yau Wong, Edmonton (CA); Baomin Tian, Edmonton (CA); Kim Gaspar, Saskatoon (CA); Marni Diane Uger, Richmond Hill (CA); Sven Rohmann, Bachs (CH); Heman Lap Man Chao, Aurora (CA)

(73) Assignee: Helix BioPharma Corp., Richmond Hill (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/712,802

(22) Filed: Sep. 22, 2017

(65) Prior Publication Data

US 2018/0087088 A1    Mar. 29, 2018

Related U.S. Application Data

(60) Provisional application No. 62/399,378, filed on Sep. 24, 2016, provisional application No. 62/554,059, filed on Sep. 5, 2017.

(51) Int. Cl.
| | | |
|---|---|---|
| *A61K 39/00* | (2006.01) | |
| *A61K 47/68* | (2017.01) | |
| *C12Q 1/58* | (2006.01) | |
| *A61K 38/20* | (2006.01) | |
| *C12N 9/00* | (2006.01) | |

(52) U.S. Cl.
CPC ............ *C12Q 1/58* (2013.01); *A61K 38/2013* (2013.01); *A61K 39/001129* (2018.08); *A61K 47/6815* (2017.08); *A61K 2039/55533* (2013.01); *C12N 9/00* (2013.01)

(58) Field of Classification Search
None
See application file for complete search history.

(56) References Cited

U.S. PATENT DOCUMENTS

| | | | |
|---|---|---|---|
| 6,261,537 B1 | 7/2001 | Klaveness et al. | |
| 7,264,800 B2 * | 9/2007 | Segal ................ | A61K 38/50 |
| | | | 424/94.6 |

FOREIGN PATENT DOCUMENTS

| | | |
|---|---|---|
| CA | 2493282 A1 | 7/2006 |
| WO | WO-2004/009112 A1 | 1/2004 |
| WO | WO-2012/040824 A1 | 4/2012 |
| WO | WO-2014/165985 A1 | 10/2014 |
| WO | WO-2016/090219 A1 | 6/2016 |
| WO | WO-2016/116907 A1 | 7/2016 |

OTHER PUBLICATIONS

Calcinotto et al., Cancer Res. Jun. 1, 2012;72(11):2746-2756 (Year: 2012).*
Yuan et al., Oncol Lett. Nov. 2016;12(5):3167-3174. Epub Sep. 9, 2016 (Year: 2016).*
"International Application No. PCT/CA2017/051116, International Search Report and Written Opinion dated Dec. 29, 2017", (Dec. 29, 2017), 9 pgs.
Tian, Baomin, et al., "Production and Characterization of a Camelid Single Domain Antibody-Urease Enzyme Conjugate for the Treatment of Cancer", Bioconjugate Chem. 2015, 26, 1144-1155, (May 4, 2015), 1144-1155.
Monga, M., et al., "Developmental Therapeutics Program at the NCI: molecular target and drug discovery process", *Leukemia*, 16(4), (2002), 520-526.
Pilon-Thomas, Shari, et al., "Neutralization of Tumor Acidity Improves Antitumor Responses to Immunotherapy", *Cancer Research*, 76(6), (2016), 1381-1390.
"International Application No. PCT/CA2017/051116, International Preliminary Report on Patentability dated Mar. 26, 2019", (Mar. 26, 2019), 8 pgs.
Wong, Wah Yau, et al., "Abstract A144: Urease-mediated alkalization of tumor microenvironment and its effects on T cell proliferation, cytokine release, and PD-1/PD-L1 interactions", Cancer Immunology Research; Abstract A144; Abstracts: Second CRI-CIMT-EATI-AACR International Cancer Immunotherapy Conference: Translating Science into Survival; Sep. 25-28, 2016; New York, NY, (Nov. 2016), 2 pgs.

* cited by examiner

*Primary Examiner* — Daniel C Gamett
(74) *Attorney, Agent, or Firm* — Schwegman Lundberg & Woessner, P.A.

(57) ABSTRACT

Methods and compositions to restore function to acidified T cells are provided. The methods comprise administering urease to the T cells. Compositions comprise urease.

23 Claims, 26 Drawing Sheets
(26 of 26 Drawing Sheet(s) Filed in Color)

RESTORING FUNCTION OF TUMOUR ACIDIFIED T CELLS

CROSS-REFERENCE TO RELATED APPLICATIONS

This application claims the benefit of priority from U.S. Provisional Application No. 62/399,378 filed Sep. 24, 2016 and U.S. Provisional Application No. 62/554,059 filed Sep. 5, 2017. The disclosures of the foregoing applications are hereby incorporated by reference in their entirety.

FIELD OF THE INVENTION

The present invention relates to dysfunctional immunity. More specifically, the present invention is, in aspects, concerned with restoring function to acidified T cells.

BACKGROUND OF THE INVENTION

The tumor microenvironment has been studied for involvement in cancer growth.

International Patent Application Publication No. WO 2004/009112 describes a pharmaceutical composition and method for use in inhibiting growth of cancer cells in a mammalian subject. The composition includes a urease enzyme, and associated therewith, a chemical entity effective to enhance the delivery of the enzyme to cancer cells, when the composition is administered to the subject. Also disclosed are a method of enhancing the effectiveness of weakly basic anti-tumor compounds, a method assessing the presence, size or condition a solid tumor in a subject, and a gene therapy composition for treating a cancer in a subject. Canadian Patent Application No. 2,493,282 describes similar compositions and methods. International Patent Application Publication No. WO 2014/165985 describes antibody-urease conjugates having therapeutic and diagnostic utility. International Patent Application Publication No. WO 2016/116907 describes pharmaceutical compositions comprising antibody-urease conjugates that are substantially free of unconjugated urease. None of these aforementioned applications describe the treatment of T cells or suggest any effects on the immune system of a subject receiving treatment.

International Patent Application Publication No. WO 2016/090219 describes inhibition of bromodomain proteins in antigen presenting cells to display lower expression of the immunosuppressive molecule PD-L1 for restoring the responsiveness of tolerant T-cells.

Pilon-Thomas et al. (Cancer Res, 2016, 76:1381-1390) describe that neutralizing tumor acidity with bicarbonate monotherapy impaired the growth of some cancer types in mice where it was associated with increased T-cell infiltration. Furthermore, combining bicarbonate therapy with anti-CTLA-4, anti-PD-1, or adoptive T-cell transfer improved anti-tumor responses in multiple models.

There is a need for alternative therapies to overcome or mitigate at least some of the deficiencies of the prior art and/or to provide the public with a useful choice for therapies.

SUMMARY OF THE INVENTION

Restoring function of T cells would be helpful for the repair of the immune system and its role in cancers. Moreover, the repair of the immune response is helpful in the treatment of tumors such as solid tumors. By targeting the T cells, the tumor can be indirectly treated.

In accordance with an aspect, there is a method for restoring/reactivating T cell function negatively affected by solid tumor growth. In aspects, the negative effect provided by acidification by the solid tumor.

In accordance with an aspect, there is provided a method to restore function/reactivate acidified T cells, the method comprising administering urease to the T cells. In aspects, the method may further comprise administering urease to cancer cells to decrease PD-L1 expression thereby reducing/minimizing the negative effects on T cell function.

In aspects the urease lowers expression of PD-1 on T cells.

In accordance with an aspect, there is provided a method to restore function/reactivate T cells, the method comprising administering urease to decrease PD-L1 expression on tumor cells, thereby restoring/reactivating T cell function.

In aspects, the cancer cells are pH sensitive.

In an aspect, restore function comprises increasing production of cytokines.

In an aspect, the cytokines comprise IL-2.

In an aspect, the T cells are acidified relative to physiological pH.

In an aspect, the T cells have a pH of less than about 7.2, such as 7.1, 7.0, 6.9, or 6.8.

In an aspect, the T cells are acidified with lactate.

In an aspect, the lactate is produced by a solid tumor.

In an aspect, the T cells are in the presence of urea, either native or administered.

In an aspect, the T cells express PD-1, optionally at higher than normal levels compared to a non-acidified T cell.

In an aspect, the urease is conjugated to a targeting moiety.

In an aspect, the targeting moiety is an antibody.

In an aspect, the antibody is specific for a tumor-associated antigen.

In an aspect, the tumor-associated antigen is CEACAM6.

In an aspect, the antibody is an AFAIKL2 antibody or a 2A3 antibody.

In an aspect, the T cells express PD-1.

In an aspect, the urease inhibits PD-1 expression and/or activation.

In an aspect, the method further comprises administering an active agent.

In an aspect, the active agent is a PD-1 inhibitor, a chemotherapeutic agent, radiation, a hormone, or a cytokine such as IL-2.

In an aspect, the method further comprises administering immunotherapy, such as adoptive T cell therapy.

In an aspect, the urease is administered in an amount sufficient to increase the pH in the vicinity of the acidified T cells to physiological levels, such as 7.2.

In an aspect, the urease is administered in an amount sufficient to decrease PD-1 expression on the T cells.

In an aspect, the urease is administered in an amount that does not cause significant T cell death or harm.

In accordance with an aspect, there is provided a method of normalizing IL-2 production by T cells subjected to acidified conditions, the method comprising administering urease to the T cells.

In accordance with an aspect, there is provided a method of inhibiting lactate-induced T cell tolerance to tumor cells, the method comprising administering urease to the T cells.

In accordance with an aspect, there is provided a method for treating cancer, the method comprising selecting subjects that have a CEACAM6+ and/or PD-L1+ cancer and administering urease to said subjects.

In accordance with an aspect, there is provided a method for increasing an immune response to a CEACAM6+ and/or PD-L1+ cancer, the method comprising administering urease to a subject comprising a CEACAM6+ and/or PD-L1+ cancer.

In accordance with an aspect, there is provided a method for increasing T cell infiltration into a solid tumor, comprising administering urease to the T cells.

In an aspect, restore function comprises increasing production of cytokines.

In an aspect, the cytokines comprise IL-2.

In an aspect, the T cells are acidified relative to physiological pH.

In an aspect, the T cells have a pH of less than about 7.2, such as 7.1, 7.0, 6.9, or 6.8.

In an aspect, the T cells are acidified with lactate.

In an aspect, the lactate is produced by a solid tumor.

In an aspect, the T cells are in the presence of urea, either native or administered.

In an aspect, the T cells express PD-1, optionally at higher than normal levels compared to a non-acidified T cell.

In an aspect, the urease is conjugated to a targeting moiety.

In an aspect, the targeting moiety is an antibody.

In an aspect, the antibody is specific for a tumor-associated antigen.

In an aspect, the tumor-associated antigen is CEACAM6.

In an aspect, the antibody is an AFAIKL2 antibody or a 2A3 antibody.

In an aspect, the T cells express PD-1.

In an aspect, the urease inhibits PD-1 expression and/or activation.

In an aspect, the method further comprises administering an active agent.

In an aspect, the active agent is a PD-1 inhibitor, a chemotherapeutic agent, radiation, a hormone, or a cytokine such as IL-2.

In an aspect, the method is in conjunction with immunotherapy, such as adoptive T cell therapy.

In an aspect, the urease is administered in an amount sufficient to increase the pH in the vicinity of the acidified T cells to physiological levels, such as 7.2.

In an aspect, the urease is administered in an amount sufficient to decrease PD-1 expression on the T cells.

In an aspect, the urease is administered in an amount that does not cause significant T cell death or harm.

In accordance with an aspect, there is provided a composition comprising urease and a PD-1 inhibitor.

In accordance with an aspect, there is provided a composition comprising or consisting of urease and a PD-1 inhibitor and/or a PDL-1 inhibitor.

In accordance with an aspect, there is provided a composition comprising or consisting of urease and T cells.

In an aspect, the composition is for restoring T cell function.

In an aspect, the composition is for increasing IL-2 production by T cells.

In accordance with an aspect, there is provided a use of urease for restoring function to acidified T cells.

In accordance with an aspect, there is provided a use of urease for normalizing IL-2 production by T cells subjected to acidified conditions.

In accordance with an aspect, there is provided a use of urease for inhibiting lactate-induced T cell tolerance to tumor cells.

In accordance with an aspect, there is provided a use of urease for treating cancer, in subjects that have a CEACAM6+ and/or PD-L1+ cancer.

In accordance with an aspect, there is provided a use of urease for increasing an immune response to a CEACAM6+ and/or PD-L1+ cancer.

In accordance with an aspect, there is provided a use of urease for increasing T cell infiltration into a solid tumor.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from said detailed description.

DESCRIPTION OF THE FIGURES

The patent or application file contains at least one drawing executed in color. Copies of this patent or patent application publication with color drawing(s) will be provided by the Office upon request and payment of the necessary fee.

The present invention will be further understood from the following description with reference to the Figures, in which:

FIG. 7(A) Untreated MDA-MB-231 cells express a moderate level of PD-L1, as determined by flow cytometry (dashed line). Treatment with IFNγ for 2 days increased PD-L1 expression. Additional treatment with L-DOS47 and urea, but not L-DOS47 alone, significantly reduced PD-L1 expression to the level of untreated cells.*** p=0.0005-0.001 compared to IFNγ treated cells. FIG. 7(B) The pH of each sample was monitored continuously throughout the experiment using PreSens SensorDishes® and SensorDish® Reader. It takes approximately 4-5 hours for the sensors and culture media to equilibrate, thus only pH measurements taken after T=5 hrs are reported. Treatment with L-DOS47 plus urea increased the pH of the media in a dose dependent manner L-DOS47 alone had no effect.

FIG. 8(A) Treatment with 12 mM lactic acid or 12 mM HCl significantly increased PD-L1 expression on IFNγ-stimulated MDA-MB-231 cells. 12 mM sodium lactate had no effect. **** p=0.0001 compared to IFNγ treated cells. FIG. 8(B) Treatment with lactic acid or HCl decreased the pH of the media in a dose dependent manner Sodium lactate had a minimal effect.

FIG. 9(A) Treatment with L-DOS47+ urea significantly decreased PD-L1 expression on MDA-MB-231 cells treated with IFNγ and 12 mM lactic acid. L-DOS47 alone had no effect. **** p=0.0001 compared to cells treated with 12 mM lactic acid. FIG. 9(B) L-DOS47+ urea treatment increased the pH of the media of cells treated with 12 mM lactic acid in a dose-dependent manner L-DOS47 alone had minimal effect.

FIG. 10 (A) Treatment with 12 mM lactic acid, 12 mM HCl or 12 mM sodium lactate had no effect on PD-L1 expression on IFNγ-stimulated SKOV-3 cells. FIG. 10(B) Treatment with lactic acid or HCl decreased the pH of the media in a dose dependent manner Sodium lactate has minimal effect.

FIG. 11(A) PD-1 levels were evaluated by flow cytometry. Activated T cells express PD-1. Levels were relatively unchanged upon treatment with L-DOS47± urea. FIG. 11(B) Treatment with L-DOS47± urea increased the pH of the media in a dose dependent manner FIG. 11(C) Treatment with L-DOS47± urea significantly increased IL-2; and FIG. 11(D) IFN-γ production from activated CD8+ T cells as measured by ELISA.

FIG. 12(A) Treatment of activated CD8+ T cells with lactic acid or HCl, but not sodium lactate, increased PD-1 expression. FIG. 12(B) Treatment with lactic acid or HCl lowered the pH of the culture media. Sodium lactate had minimal effect. FIG. 12(C) Treatment with HCl significantly reduced IL-2 production and treatment with sodium lactate significantly increased IL-2 production by activated CD8+ T cells. Treatment with lactic acid had no effect. ** p=0.0001 compared to activated CD8+ T cells. FIG. 12(D) Both lactic acid and HCl treatments significantly impaired IFNγ production by activated CD8+ T cells. Sodium lactate had no effect. ** p=0.0001 compared to activated CD8+ T cells.

FIG. 13(A) Treatment with L-DOS47+ urea, but not L-DOS47 alone, reduced PD-1 expression on lactic acid-treated activated CD8+ T cells. FIG. 13(B) L-DOS47± urea treatment increased the pH of the culture media. FIG. 13(C) Treatment with L-DOS47+ urea, but not L-DOS47 alone, significantly increased IL-2 production by lactic acid-treated activated CD8+ T cells.  p=0.0014,  p=0.0001 compared to lactic acid-treated activated CD8+ T cells. FIG. 13(D) Treatment with L-DOS47± urea significantly increased IFNγ production by lactic acid-treated activated CD8+ T cells. ** p=0.0001 compared to lactic acid-treated activated CD8+ T cells. L-DOS47+4 mM urea restored IFNγ production to levels generated by activated CD8+ T cells (no statistically significant difference observed between these two groups).

DETAILED DESCRIPTION

Figure 1:
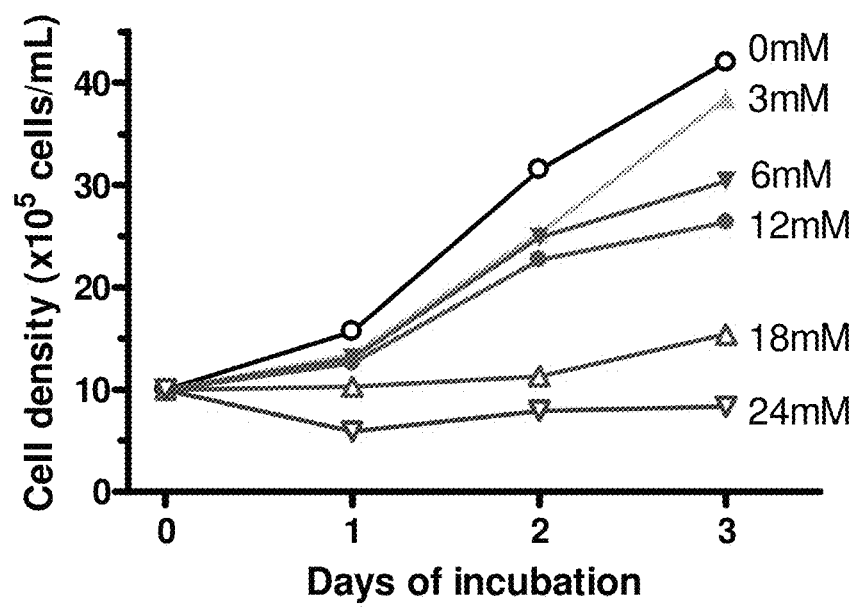
FIG. 1. Effects of lactic acid on Jurkat cell proliferation. Jurkat cells ($1 \times 10^6$ cells/mL) were incubated in complete RPMI 1640 medium containing various amounts of lactic acid (3 to 24 mM) for 1-3 days. Cell count was performed using a hemocytometer after Trypan Blue staining. The results show that lactic acid prohibits Jurkat cell proliferation at concentrations >3 mM. A similar growth inhibition profile was observed when lactic acid was replaced with the same concentrations of HCl (data not shown).

The patent or application file contains at least one drawing executed in color. Copies of this patent or patent application publication with color drawing(s) will be provided by the Office upon request and payment of the necessary fee.

Solid tumors become ischemic due to a reduced blood supply and have abnormal metabolic processes. As a consequence, lactate levels tend to be higher than normal within and around tumors and the pH tends to be low. It has previously been shown that urease, conjugated to a tumor-specific antibody, is capable of raising the pH in the tumor microenvironment and reduce tumor growth. These effects were based on targeting a urease moiety directly to the tumor by conjugating the urease to a tumor-specific targeting moiety in order to directly target and treat the tumor and cancer cells.

Now, it is shown that acidity, in aspects tumor-induced acidity and, further in aspects, tumor produced lactate, affects T cells by suppressing cytokine release. This dampens the ability of T cells to attack tumor cells and elicit an effective immune response, rendering the T cells tolerant to the tumor. Described herein is data showing that urease, alone or conjugated to a tumor-specific antibody, is capable of reversing at least in part the dampening effect of acidity and/or lactate on T cell cytokine release. This restores normal T cell function, reactivating the immune response against the tumor and reversing the tolerogenic effect of the acidity and/or lactate. This provides novel methods, uses and compositions for the treatment of T cells negatively affected by acidity, in aspects tumor derived acidity.

In the methods of the invention, the reactivation and function of T cells can be further restored by reducing PD-L1 expression on tumor cells (in aspects acid sensitive tumor cells) and also in aspects PD-1 expression on CD8+ T cells using such described antibody-urease conjugate, which in some aspects is L-DOS47. L-DOS47 has urease conjugated to a camelid single domain antibody specific for human CEACAM6.

While the aforementioned references describe treating a tumor directly via cancer cell targeting, described herein are methods and compositions that treat (i.e. positively affect) T cells to make a stronger T cell population (i.e. produce cytokines and recruit more T cells) that is capable of recognizing and attacking tumor cells.

Definitions

As used herein, "treatment" or "therapy" is an approach for obtaining beneficial or desired clinical results. For the purposes described herein, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" and "therapy" can also mean prolonging survival as compared to expected survival if not receiving treatment or therapy. Thus, "treatment" or "therapy" is an intervention performed with the intention of altering the pathology of a disorder. Specifically, the treatment or therapy may directly prevent, slow down or otherwise decrease the pathology of a disease or disorder such as an infection, or may render the cells more susceptible to treatment or therapy by other therapeutic agents.

The terms "therapeutically effective amount", "effective amount" or "sufficient amount" mean a quantity sufficient, when administered to a subject, including a mammal, for example a human, to achieve a desired result, for example an amount effective to treat an infection. Effective amounts of the compounds described herein may vary according to factors such as the disease state, age, sex, and weight of the subject. Dosage or treatment regimens may be adjusted to provide the optimum therapeutic response, as is understood by a skilled person.

Moreover, a treatment regime of a subject with a therapeutically effective amount may consist of a single administration, or alternatively comprise a series of applications. The length of the treatment period depends on a variety of factors, such as the severity of the disease, the age of the subject, the concentration of the agent, the responsiveness of the patient to the agent, or a combination thereof. It will also be appreciated that the effective dosage of the agent used for the treatment may increase or decrease over the course of a particular treatment regime. Changes in dosage may result and become apparent by standard diagnostic assays known in the art. The compounds described herein may, in aspects, be administered before, during or after treatment with conventional therapies for the disease or disorder in question, such as an infection.

The term "cancer" is meant to refer to an abnormal cell or cells, or a mass of tissue. The growth of these cells or tissues exceeds and is uncoordinated with that of the normal tissues or cells, and persists in the same excessive manner after cessation of the stimuli which evoked the change. These neoplastic tissues or cells show a lack of structural organization and coordination relative to normal tissues or cells which may result in a mass of tissues or cells which can be either benign or malignant. As used herein, cancer includes any neoplasm. This includes, but is not limited to, melanoma, adenocarcinoma, malignant glioma, prostatic carcinoma, kidney carcinoma, bladder carcinoma, pancreatic carcinoma, thyroid carcinoma, lung carcinoma, colon carcinoma, rectal carcinoma, brain carcinoma, liver carcinoma, breast carcinoma, ovary carcinoma, and the like. In particular aspects, the cancers express PD-L1 and/or CEACAM6. In other particular aspects, the cancers are solid tumors.

A "tumor" or "solid tumor" refers to a cohesive mass of cancer cells, including but not limited to semi-solid and solid tumors, solid tumor metastases, angiofibromas, retrolental fibroplasia, hemangiomas, and Karposi's sarcoma.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

More specifically, the term "inhibit" in relation to the growth of cancer cells refers to any slowing of the rate of cancer cell proliferation and/or migration, arrest of cancer cell proliferation and/or migration, or killing of cancer cells, such that the rate of cancer cell growth is reduced in comparison with the observed or predicted rate of growth of an untreated control cancer cell. The term "inhibits growth" can also refer to a reduction in size or disappearance of a cancer cell or tumor, as well as to a reduction in its metastatic potential. Preferably, such an inhibition at the cellular level may reduce the size, deter the growth, reduce the aggressiveness, or prevent or inhibit metastasis of a cancer in a patient. Those skilled in the art can readily determine, by any of a variety of suitable indicia, whether cancer cell growth is inhibited.

Inhibition of cancer cell growth may be evidenced, for example, by arrest of cancer cells in a particular phase of the cell cycle, e.g., arrest at the G2/M phase of the cell cycle. Inhibition of cancer cell growth can also be evidenced by direct or indirect measurement of cancer cell or tumor size. In human cancer patients, such measurements generally are made using well known imaging methods such as magnetic resonance imaging, computerized axial tomography and X-rays. Cancer cell growth can also be determined indirectly, such as by determining the levels of circulating carcinoembryonic antigen, prostate specific antigen or other cancer-specific antigens that are correlated with cancer cell growth. Inhibition of cancer growth is also generally correlated with prolonged survival and/or increased health and well-being of the subject.

"Reversal" (or "reverse") of a state or condition and "restoration" (or "restore" or "reactivate") of function encompasses both complete and partial reversal or restoration unless otherwise stated. In particular aspects, reversal and/or restoration/reactivation refer to the ability of T cells to produce and release cytokines such as but not limited to IL-2. Thus restoration in an aspect encompasses repair of the immune system with respect to acid-sensitive T cells (susceptible to the negative effects of tumor induced acidity).

The term "urease" refers to an enzyme having the enzymatic activity of a urea amidohydrolase (E.G. 3.5.1.5), either naturally occurring or obtained by e.g., recombinant nucleic acid techniques and/or chemical synthesis. Urease also includes fusion proteins comprising the entire urease, subunits, or fragments thereof, and/or urease with amino acid substitutions, deletions or additions that preserve the urea amidohydrolase activity of the polypeptide. A truncated urease sequence as used herein is a fragment of urease that is free from a portion of the intact urease sequence beginning at either the amino or carboxy terminus of urease. Methods for isolating native urease, for synthesizing urease recombinantly, and for identifying active fragments and modified urease polypeptides are described in detail in International Patent Application Publication No. WO 2004/009112, incorporated herein by reference in its entirety.

As used herein, the term "targeting moiety" refers to a molecule that binds to a defined population of cells or selected cell type. The targeting moiety may bind a receptor, an oligonucleotide, an enzymatic substrate, an antigenic determinant, or other binding site present on or in the target cell or cell population. An exemplary targeting moiety is an antibody. Antibody fragments and small peptide sequences capable of recognizing expressed antigens are also contemplated targeting moieties.

The terms "subject", "individual" and "patient" are used interchangeably herein to refer to any target of the treatment. Also provided by the present invention is a method of treating tumor cells in situ, or in their normal position or location, for example, neoplastic cells of breast or prostate tumors. These in situ tumors can be located within or on a wide variety of hosts; for example, human hosts, canine hosts, feline hosts, equine hosts, bovine hosts, porcine hosts, and the like. Any host in which is found a tumor or tumor cells can be treated and is in accordance with the present invention. A subject thus includes a vertebrate, preferably a mammal, more preferably a human.

Administration "in combination with" one or more further therapeutic agents includes simultaneous (concurrent) and consecutive administration in any order.

The term "pharmaceutically acceptable" means that the compound or combination of compounds is compatible with the remaining ingredients of a formulation for pharmaceutical use, and that it is generally safe for administering to humans according to established governmental standards, including those promulgated by the United States Food and Drug Administration.

The term "pharmaceutically acceptable carrier" includes, but is not limited to solvents, dispersion media, coatings, antibacterial agents, antifungal agents, isotonic and/or absorption delaying agents and the like. The use of pharmaceutically acceptable carriers is well known.

Included herein are pharmaceutically acceptable salts, solvates and prodrugs of the compounds described herein and mixtures thereof.

In understanding the scope of the present application, the articles "a", "an", "the", and "said" are intended to mean that there are one or more of the elements. Additionally, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

It will be understood that any aspects described as "comprising" certain components may also "consist of" or "consist essentially of," wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effect(s) described herein. For example, a composition defined using the phrase "consisting essentially of" encompasses any known pharmaceutically acceptable additive, excipient, diluent, carrier, and the like. Typically, a composition consisting essentially of a set of components will comprise less than 5% by weight, typically less than 3% by weight, more typically less than 1% by weight of non-specified components.

It will be understood that any component defined herein as being included may be explicitly excluded from the claimed invention by way of proviso or negative limitation. For example, in aspects, bicarbonate and/or an oral buffer is explicitly excluded from the compositions and methods described herein. In other aspects, a tumor-specific targeting moiety is not included in the compositions described herein and/or is not conjugated to the urease moiety.

In addition, all ranges given herein include the end of the ranges and also any intermediate range points, whether explicitly stated or not.

Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

Urease

The compositions and methods described here comprise urease. It will be understood that any suitable urease may be used in the compositions and methods described herein. For example, WO 2004/009112 (incorporated herein by reference in its entirety) describes many different types of ureases derived from many different sources. Any of the ureases described in that application may equally be used in the present application. Typically the urease is jack bean urease.

In some aspects, the urease is for use unconjugated to another moiety. Urease may be provided directly to/around the tumor milieu via intratumoral injection or injection surrounding/near the tumor. For example, the urease may be targeted and/or directly administered to the surrounding stroma. The urease may also be targeted to the desired T cells using gene therapy.

In other aspects, the urease is conjugated to a targeting moiety as described below. In yet other aspects, the urease is enclosed in liposomes or is associated with nanoparticles.

Targeting Moieties

The urease is in aspects typically conjugated to a targeting moiety. Targeting moieties bind to a defined, selected cell type or target cell population, such as cancer cells. Targeting moieties useful in this regard include, for example, antibodies and antibody fragments, peptides, and hormones. Proteins corresponding to known cell surface receptors (including low density lipoproteins, transferrin and insulin), fibrinolytic enzymes, anti-HER2, platelet binding proteins such as annexins, and biological response modifiers (including interleukin, interferon, erythropoietin and colony-stimulating factor) are also contemplated targeting moieties. Additionally targeting moieties are described in detail in WO 2004/009112 (incorporated herein by reference). In typical aspects, the targeting moiety is an antibody or fragment thereof that targets the urease to a tumor via a tumor-specific antigen such as CEACAM6. Exemplary CEACAM6 targeting moieties are described in International Patent Application Publication Nos. WO 2016/116907 or WO 2012/040824 (each of which is incorporated herein by reference in its entirety). In other aspects, the targeting moiety may target the T cells specifically via PD-1. In other aspects, the targeting moiety may target the acidic environment in and/or around the tumor via lactate.

Compositions

The compositions described herein can be prepared by per se known methods for the preparation of pharmaceutically acceptable compositions that can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, 20th ed., Mack Publishing Company, Easton, Pa., USA, 2000). On this basis, the compositions may include, albeit not exclusively, the urease, along or in combination with a targeting moiety, and in association with one or more pharmaceutically acceptable vehicles or diluents, and may be contained in buffered solutions with a suitable pH that are iso-osmotic with physiological fluids.

In specific aspects, the compositions described herein may be for use in immunotherapy and may comprise urease (alone or conjugated to a targeting moiety) for administration to the T cells of a subject. The T cells may be in vivo, ex vivo or in vitro. In aspects the urease compositions are administered to a subject to restoring the function to acidified T cells in said subject.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of the subject. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions. The pharmaceutical composition may be supplied, for example, but not by way of limitation, as a lyophilized powder which is reconstituted with sterile water or saline prior to administration to the patient.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1 (2,3-dioleyloxy)propyl)N,N,N-trimethylammonium chloride (DOTMA), diolesylphosphotidyl-ethanolamine (DOPE), and liposomes. Such compositions should contain a therapeutically effective amount of the active agent, together with a suitable amount of carrier so as to provide the form for direct administration to the patient.

Additional active agents may also be included in the composition of the invention. The additional active agents, e.g., an anti-tumor agent (an agent active against proliferating cells), may be utilized in the composition prior to, concurrently with, or subsequent to the cells being contacted with a first active agent. For example, after urease has been targeted to the tumor and/or T cells and/or acidic milieu and/or stroma, it may have the ability to modulate or regulate the tumor external environment, e.g., through pH changes. Active agents, e.g., anti-tumor agents that favor a basic environment will then be more efficacious. In certain embodiments, substrates that are capable of being enzymatically processed by urease are contemplated for use as active agents. Preferably, the active agent is a substrate that urease may utilize to form ammonium ions, e.g., urea.

Exemplary anti-tumor agents include cytokines and other moieties, such as interleukins (e.g., IL-2, IL-4, IL-6, IL-2 and the like), transforming growth factor-beta, lymphotoxin, tumor necrosis factor, interferons (e.g., gamma-interferon), colony stimulating factors (e.g., GM-CSF, M-CSF and the like), vascular permeability factor, lectin inflammatory response promoters (selectins), such as L-selectin, E-selectin, P-selectin, and proteinaceous moieties, such as C1 q and NK receptor protein. Additional suitable anti-tumor agents include compounds that inhibit angiogenesis and therefore inhibit metastasis. Examples of such agents include protamine medroxyprogesteron, pentosan polysulphate, suramin, taxol, thalidomide, angiostatin, interferon-alpha, metalloproteinase-inhibitors, platelet factor 4, somatostatin, thromobospondin. Other representative and non-limiting examples of active agents useful in accordance with the invention include vincristine, vinblastine, vindesine, busulfan, chlorambucil, spiroplatin, cisplatin, carboplatin, methotrexate, adriamycin, mitomycin, bleomycin, cytosine arabinoside, arabinosyl adenine, mercaptopurine, mitotane, procarbazine, dactinomycin (antinomycin D), daunorubicin, doxorubicin hydrochloride, taxol, plicamycin, aminoglutethimide, estramustine, flutamide, leuprolide, megestrol acetate, tamoxifen, testolactone, trilostane, amsacrine (m-AMSA), asparaginase (L-asparaginase), etoposide, blood products such as hematoporphyrins or derivatives of the foregoing. Other examples of active agents include genetic material such as nucleic acids, RNA, and DNA of natural or synthetic origin, including recombinant RNA and DNA. DNA encoding certain proteins may be used in the treatment of many different types of diseases. For example, tumor necrosis factor or interleukin-2 genes may be provided to treat advanced cancers; thymidine kinase genes may be provided to treat ovarian cancer or brain tumors; and interleukin-2 genes may be provided to treat neuroblastoma, malignant melanoma or kidney cancer. Additional active agents contemplated for use in the present invention are described in U.S. Pat. No. 6,261,537, which is incorporated by reference in its entirety herein. Anti-tumor agents and screens for detecting such agents are reviewed in Monga, M. and Sausville, E. A. (2002) Leukemia 16(4):520-6.

In certain embodiments, the active agent is a weakly basic anti-tumor compound whose effectiveness is reduced by a higher intracellular/lower extracellular pH gradient in a solid tumor. Exemplary weakly basic anti-tumor compounds include doxorubicin, daunorubicin, mitoxanthrone, epirubicin, mitomycin, bleomycin, vinca alkaloids, such as vinblastine and vincristine, alkylating agents, such as cyclophosphamide and mechlorethamine hydrochloride, and antineoplastic purine and pyrimidine derivatives.

In one aspect, the composition includes urease, and lacks substantially any cytokines, e.g. tumor necrosis factor and/or interferons. In this embodiment, urease alone, or with active agents other than cytokines, typically in combination with small molecule anti-tumor agents, is effective to help restore normal T cell function. Thus, in this aspect, the composition may or may not act in concert with endogenous or native cytokines present in the subject being treated, but the composition being administered does not contain additional, exogenous cytokines.

In other aspects, the additional active agent is a PD-1 inhibitor.

PD-1 inhibitors may include antibodies to PD-1 such as nivolumab and pembrolizumab.

Kits

In still another aspect, this invention provides kits for restoring T cell function using the methods described herein. The kits include a container containing one or more active agents. The kits can additionally include any of the other components described herein for the practice of the methods of this invention. Such components include, but are not limited to pharmaceutical components, targeting moieties, imaging agents, clearing agents, gene therapy components, and the like.

The kits may optionally include instructional materials containing directions (i.e., protocols) disclosing the use of active agents for restoring T cell function. Thus, in one embodiment, the kit includes a pharmaceutical composition containing an active agent, preferably a urease enzyme, and instructional materials teaching the administration of the composition to a subject, for the treatment of a cancer in the subject. In one embodiment, the instructional material teaches administering the urease composition to a subject in an amount—which is dependent on the size of the tumor and between 0.1 to 100 international units urease activity per $mm^3$ tumor, when the composition is administered by direct injection into the tumor, and in an amount between 100-100,000 international units/kg international units urease activity/kg subject body weight, when the composition is administered parenterally to the subject other than by direct injection into the tumor.

In another embodiment, the instructional material teaches administering the urease composition to a subject who is also receiving a weakly basic anti-tumor compound whose effectiveness is reduced by a higher intracellular/lower extracellular pH gradient in a solid tumor, in an amount of urease effective to reduce or reverse the higher intracellular/lower extracellular pH gradient in a solid tumor.

Alternatively, the instructional material teaches administering the urease composition to a subject containing, or suspected of containing, a solid tumor that creates an acidic environment that acidifies T cells, under conditions effective to localize the urease to the Tcells in the vicinity of the tumor in the subject, interrogating the subject with a diagnostic tool capable of detecting changes in extracellular pH in a subject's tissue, and identifying a tissue region within the subject that shows an elevation in extracellular pH following said administering. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

Methods of Treatment

As described herein, the urease alone or conjugated to a targeting moiety may find use in restoring T cell function, reducing T cell tolerance, increasing T cell infiltration into a solid tumor, and/or promoting cytokine release from T cells.

It is contemplated that the compositions described herein may be used in combination with conventional treatments for cancer, such as surgery, chemotherapy, hormone therapy, radiation, and/or immunotherapy, resulting in aspects, in an additive or synergistic treatment modality. The compositions herein may be used in conjunction with adoptive T cell therapy whereby T cells are collected from a patient and grown in the laboratory which are then given back to the patient to help the immune system fight disease. Also called cellular adoptive immunotherapy.

The compositions described herein can, in aspects, be administered for example, by parenteral, intravenous, subcutaneous, intradermal, intramuscular, intracranial, intraorbital, ophthalmic, intraventricular, intracapsular, intraspinal, intracisternal, intraperitoneal, intranasal, intrarectal, aerosol or oral administration. Typically, the compositions described herein are administered subcutaneously, intramuscularly, or intradermally. More typically, the compositions described herein are administered by injection.

The compositions described herein may, in aspects, be administered in combination, concurrently or sequentially, with conventional treatments for cancer, as described above. The compositions may be formulated together with such conventional treatments when appropriate. For example, the compositions may be administered prior to conventional treatments so that the cancer cells and/or T cells are rendered more susceptible to the conventional treatments.

The compositions described herein may be used in any suitable amount, but are typically provided in doses comprising from about 0.001 μM to about 1000 μM agonist, such as from about 0.001 μM, about 0.01 μM, about 0.1 μM, about 1 μM, about 10 μM, or about 100 μM to about 0.01 μM, about 0.1 μM, about 1 μM, about 10 μM, about 100 μM, or about 1000 μM agonist. Alternatively, the compositions described herein may be administered in doses such as from about 0.001 mg/kg to about 1000 mg/kg, such as from about 0.001 mg/kg, about 0.01 mg/kg, about 0.1 mg/kg, about 1 mg/kg, about 10 mg/kg, or about 100 mg/kg to about 0.01 mg/kg, about 0.1 mg/kg, about 1 mg/kg, about 10 mg/kg, about 100 mg/kg, or about 1000 mg/kg.

In other aspects, where a urease composition is injected in the vicinity of a tumor and/or directly into a tumor, an exemplary dose is 0.1 to 1,000 international units urease activity per $mm^3$ tumor. For example, and assuming a relatively uniform distribution of the urease in the tumor is achieved, a dose of between 0.5 and 5 international units may be suitable. The placement of the injection needle may be guided by conventional image guidance techniques, e.g., fluoroscopy, so that the physician can view the position of the needle with respect to the target area, or target tissue. Such guidance tools can include ultrasound, fluoroscopy, CT or MRI.

In accordance with one aspect of the invention, the effectiveness or distribution of the administered urease dose may be monitored, during or after direct injection of urease into the vicinity of the tumor, by monitoring the tumor tissue by a tool capable of detecting changes in pH within the cancerous tissue region of the subject. Such tools may include a pH probe that can be inserted directly into the tumor, or a-visualization tool, such as magnetic resonance imaging (MRI)—computerized tomography (CT), or fluoroscopy. MRI interrogation may be carried out in the absence of additional imaging agents, based simply on differences in magnetic properties of tissue as a function of pH, CT or fluoroscopic imaging may require an additional pH-sensitive imaging agent whose opacity is affected by the pH of the tissue medium. Such agents are well known to those of skill in the art.

Before any urease injection, the tumor tissue can be visualized by its lower pH relative to surrounding normal tissue. Thus, the normal tissue may have a normal pH of about 7.2, whereas the tumor tissue may be 0.1 to 0.4 or more pH units lower. That is, before any urease is injected, the extent of tumor tissue can be defined by its lower pH. Following urease administration, the pH of the tumor region having urease will begin to rise, and can be identified by comparing the resulting images with the earlier pre-dosing images.

By interrogating the tissue in this manner, the degree of change in pH and extent of tissue affected may be monitored. Based on this interrogation, the physician may administer additional composition to the site, and/or may administer composition at additional areas within the tumor site. This procedure may be repeated until a desired degree of pH changes, e.g., 0.2 to 0.4 pH units, has been achieved over the entire region of solid tumor.

Dosing by direct injection may be repeated by suitable intervals, e.g., every week or twice weekly, until a desired end point, preferably substantial or complete regression of tumor mass is observed. The treatment efficacy can be monitored, as above, by visualizing changes in the pH of the treated tissue during the course of treatment. Thus, before each additional injection, the pH of the tissue can be visualized to determine the present existing extent of tumor, after which changes in the pH of the tissue can be used to monitor the administration of the new dose of urease composition to the tissue.

Where the urease is administered parenterally by a method other than direct injection, an exemplary dose of the urease is 100-100,000 international units/kg urease activity/kg subject body weight. As noted herein, the urease composition in this method preferably includes a targeting agent for targeting urease to the cancer cells and/or T cells and/or acidic microenvironment, e.g., site of solid tumor, or for sequestering urease, e.g., in liposomal form, selectively at the tumor site.

Additionally, treatment with the compositions described herein may occur once or may be repeated several times. For example, treatment may occur daily, weekly, monthly, yearly, or a combination thereof, depending upon the disease state. For example, a subject may be administered several doses on an hourly, daily, or weekly basis in order to treat an active cancer. Once the cancer slows or goes into remission, follow-up maintenance doses may be provided, for example, on a monthly basis, every three months, every six months, or on a yearly basis.

In an aspect, urease or a urease containing composition is administered to a solid tumor or in the vicinity of a solid tumor in an amount effective to raise the extracellular pH of the tumor fluid at least 0.1 pH unit, e.g., 0.1 to 0.5 pH units or more. In certain embodiments, the extracellular pH of the fluid is raised to at least pH 7.0, 7.2, or higher to restore acidified T cell function.

The urease may be administered as described above, e.g., directly into the subject's tumor or parenterally other than by direct injection to restore acidified T cell function. Also as described above, the change in pH produced by the administration of urease may be monitored by determining changes in pH in tumor tissue and around tumor tissue and the extent of those changes, using imaging tools for visualizing tumor pH, or by direct pH measurements of the tumor. Changes in T cell proliferation and production of cytokines can be determined.

The dose administered in this method may be less than that needed where urease is the sole anti-tumor agent, as long as the amount injected is sufficient to produce the desired rise in tumor pH. Alternatively, the method may involve administration of a therapeutic amount of urease and a therapeutic or sub-therapeutic amount of the anti-cancer compound or other active agent. As can be appreciated, the method may allow a lower than normal dose of the anti-cancer compound or other active agent to be given, both because urease may enhance the therapeutic effect of the compound, and because urease is itself contributing to the therapeutic effect. In aspects, greater efficacy with fewer side effects result.

In one aspect, a chemical entity, as described above, may also be associated with the active agent to enhance the delivery of the active agent. In this embodiment, the active agent may be administered by any method, e.g., parenterally, other than direct injection.

Aspects of the invention include:
1. A method for restoring function to acidified T cells, the method comprising administering urease to the T cells.
2. The method of aspect 1, wherein restoring function comprises increasing production of cytokines.
3. The method of aspect 2, wherein the cytokines comprise IL-2.
4. The method of aspect 1, wherein the T cells are acidified relative to physiological pH such that the T cells have a pH of less than about 7.2, less than about 7.1, less than about 7.0, less than about 6.9, or less than about 6.8.
5. The method of aspect 4, wherein the T cells are acidified with lactate produced by a solid tumor.
6. The method of aspect 1, wherein the T cells are in the presence of urea, either native or administered.
7. The method of aspect 1, wherein the T cells express PD-1, optionally at higher than normal levels compared to a non-acidified T cell and wherein the urease inhibits PD-1 expression and/or activation.
8. The method of aspect 1, wherein the urease is conjugated to a targeting moiety.
9. The method of aspect 8, wherein the targeting moiety is an antibody specific for a tumor-associated antigen.
10. The method of aspect 8, wherein the tumor-associated antigen is CEACAM6.
11. The method of aspect 10, wherein the antibody is an AFAIKL2 antibody or a 2A3 antibody.
12. The method of aspect 1, wherein the urease inhibits PD-L1 expression on acid sensitive cancer cells.
13. The method of aspect 1, further comprising administering to said acidified T cells an active agent selected from a PD-1 inhibitor, a chemotherapeutic agent, radiation, a hormone, a cytokine such as IL-2 and combinations thereof.
14. The method of aspect 1, in conjunction with immunotherapy, such as adoptive T cell therapy.
15. The method of aspect 1, wherein the urease is administered in an amount sufficient to increase the pH in the vicinity of the acidified T cells to physiological levels, such as 7.2.
16. The method of aspect 15, wherein the urease is administered in an amount sufficient to decrease PD-1 expression on the T cells.
17. The method of aspect 1, wherein the urease is administered in an amount that does not cause significant T cell death or harm.
18. A method of normalizing IL-2 production by T cells subjected to acidified conditions, the method comprising administering urease to the T cells.
19. A method of inhibiting lactate-induced T cell tolerance to tumor cells, the method comprising administering urease to the T cells.
20. A method for increasing an immune response to a CEACAM6+ and/or PD-L1+ cancer by reactivating acidified T cells, the method comprising administering urease to a subject having a CEACAM6+ and/or PD-L1+ cancer.
21. The method of aspect 20, wherein said urease increases T cell infiltration into said cancer, said cancer being a solid tumor.

22. A composition comprising or consisting of urease and optionally a PD-1 inhibitor and/or a PDL-1 inhibitor for restoring T cell function.

23. The composition of aspect 22, wherein said composition increases IL-2 production by T cells.

EXAMPLES

The following examples are given for the purpose of illustrating various aspects of the disclosure. They are not meant to limit the disclosure in any fashion. One skilled in the art will appreciate that the disclosure is well adapted to carry out the objects and obtain the ends and advantages mentioned, as well any objects, ends and advantages inherent herein. The present examples (along with the methods described herein) are presently representative of preferred aspects. They are exemplary, and are not intended as limitations on the scope of the disclosure. Variations and other uses which are encompassed within the spirit of the disclosure as defined by the scope of the claims will occur to those skilled in the art. Changes in form and substitution of equivalents are contemplated as circumstances may suggest or render expedient. Although specific terms have been employed herein, such terms are intended in a descriptive sense and not for purpose of limitation.

Introduction

Solid tumors become ischemic due to a reduced blood supply and abnormal metabolic processes. As a consequence, lactate levels tend to be higher than normal within and around tumors and the pH tends to be low. The acidic microenvironment is key for cancer progression as it promotes the invasiveness and metastatic behaviors of cancer cells. In addition, it protects cancer cells from immunotherapy by suppressing the proliferation and cytotoxic activities of local immune effector cells. Described herein is a novel method to restore T cell function, using urease, in aspects as the antibody-urease conjugate, L-DOS47.

L-DOS47 is currently in Phase I/II testing for treatment of non-small cell lung cancer. It is prepared by conjugating urease to a camelid single domain antibody specific for human CEACAM6. The immunoconjugate specifically targets and delivers urease to CEACAM6-expressing cancer cells, where the urease enzyme converts urea into cytotoxic ammonia. The ammonia also increases the pH of the tumor microenvironment in situ.

In this study, L-DOS47 was used to augment the extracellular pH of acidified culture media that mimics the tumor microenvironment in vitro, and the effects on the human T lymphoblastoid cell line, Jurkat Clone E6-1, were examined.

Example 1—Effects of Lactic Acid on Jurkat Cell Proliferation

Materials
1. Advanced RPMI-1640 medium containing 5% FBS, Glutamax, and antibiotics
2. Lactic acid, 6.03 M
3. Trypan blue solution, 0.4% (w/v) in PBS Procedures
1. Medium supplemented with 1.5 to 24 mM lactic acid was prepared;
2. Jurkat cells were prepared and 500 µL/well of cells (final cell no. is 9.3×10$^5$ cells/well) were added to corresponding wells containing 1 mL medium;
3. The plate was incubated at 37° C. and 5% $CO_2$;
4. On Day 1, 2, and 3, 80 µL of cell culture was taken from each well and cells were counted by adding 20 µL of Trypan blue solution.

Results

First, it was determined how much urea was required to be included in the experiments in order to restore the pH of lactic-acid treated medium to physiological levels through use of L-DOS-47. Hydrolysis of urea by the urease moiety of L-DOS47 produces ammonia $[(NH_2)2CO+H_2O \rightarrow CO_2 + 2NH_3]$, which converts into ammonium ions and augments the pH in aqueous medium $[NH_3+H_2O \rightarrow NH_4^+ +OH^-]$.

The data in Table 1, below, show that in the presence of 1 µg/mL L-DOS47, 2-4 mM of urea was sufficient to restore the pH of lactic acid-treated RMPI 1640 medium (supplemented with 5% heat-inactivated FBS and GlutaMax) to physiological levels after an 18-hour incubation at 37° C. and 5% $CO_2$.

TABLE 1

Effect of urea on pH in the presence of L-DOS47.

| Lactic acid (mM) | pH | | | | | |
|---|---|---|---|---|---|---|
| | | | 1 µg/mL L-DOS47 (Time 18 h) | | | |
| | Time 0 | Time 18 h | No urea | 2 mM urea | 4 mM urea | 8 mM urea |
| 0 | 7.58 | 7.22 | 7.39 | 7.45 | 7.55 | 8.16 |
| 6 | 7.03 | 7.24 | 7.32 | 7.43 | 7.52 | 7.66 |
| 12 | 6.53 | 6.99 | 7.21 | 7.34 | 7.45 | 7.60 |

Next, the effects of lactic acid on Jurkat cell proliferation were measured. Jurkat cells (1×10$^6$ cells/mL) were incubated in complete RPMI 1640 medium containing various amounts of lactic acid (3 to 24 mM) for 1-3 days. Cell count was performed using a hemocytometer after Trypan Blue staining. The results show that lactic acid prohibits Jurkat cell proliferation at concentrations ≥3 mM (FIG. 1). A similar growth inhibition profile was observed when lactic acid was replaced with the same concentrations of HCl (data not shown).

Example 2—Effects of Lactic Acid on IL-2 Release in Activated Jurkat Cells

Materials
1. Advanced RPMI-1640 medium containing 5% heat-inactivated FBS (HIFBS), Glutamax, and antibiotics
2. Cell stimulation reagents:
   Phorbol 12-myristate 13-acetate (PMA), 5 µg/mL, Abcam cat # AB120297
   Ionomycin, 1 mg/mL DMSO, Abcam cat # AB120116-2
   Phytohemagglutinin (PHA), 2 mg/mL, Sigma cat # L8754)
3. Lactic acid, 6.03 M Procedures
1. Jurkat cells were prepared at a final cell concentration of 5×10$^6$ cells/mL;
2. Either 3, 2, 1, or 0.5 µL of lactic acid was added to a corresponding well containing 1 mL of cell culture to a final concentration of 18, 12, 6, and 3 mM, respectively;
3. 1.25 µL of PHA (final: 2.5 µg/mL), 10 µL PMA (final: 50 ng/mL), and 0.75 µL Ionomycin (final 0.75 µg/mL) were added to the wells;
4. The plate was incubated at 37° C. for 24 hrs;
5. Cell culture was transferred to Eppendorf tubes and centrifuged at 7000 rpm for 10 min to collect supernatant;

6. ELISA was performed to determine the amount of IL-2 released by Jurkat cells.

IL-2 ELISA Materials
1. Bovine Serum albumin (BSA), Roche REF10735086001
2. Human IFN-gamma DuoSet ELISA, R&D Systems, Cat # DY285:
Human IL-2 Capture Antibody, Part #840104
Human IL-2 Detection Antibody, Part #840105
Human IL-2 standard, Part #840106
Streptavidin-HRP, Part #893975
3. ELISA plate, 96 well EIA/RIA Plate, Costar 3590
4. TMB (3,3',5,5'-Tetramethylbenzidine, Aldrich, 860336-1G)
5. Dimethyl sulfoxide, Sigma, D8418-50 ml
6. Hydrogen Peroxide, 30%, Fisher H325-500
7. PBS, pH 7.2-7.4
8. Wash Buffer: 0.05% Tween® 20 in PBS, pH 7.2-7.4
9. Block Buffer: 3% BSA in PBS, pH 7.2-7.4, 0.2 µm filtered
10. Reagent Diluent: 0.1% BSA, 0.05% Tween 20 in PBS, 0.2 µm filtered.
11. Acetate-citrate buffer: weigh 14.7 g sodium citrate tribasic, and dissolve in 500 ml water. Adjust the pH to 4.5 using glacial acetic acid
12. TMB stock solution: Weigh 93.0 mg of TMB in 4 ml DMSO, store in dark (stable for 1 Month at RT)
13. Substrate Solution: Just before use, mix 6.0 ml Color Reagent A ($H_2O_2$) and 6.0 ml Color Reagent B (Tetramethylbenzidine) in a 15 ml screw-caped tube.
14. Stop Solution: 2 N H2SO4. Dilute 5.6 ml $H_2SO_4$ (36N) to 100 ml water. Lot #160330ST
15. Human IL-2 standard stock solution (60 ng/mL). Add 0.500 ml Regent diluent to the vial of the IL-2 vial. Close the cap and gently flip over the vial to dissolve the protein. Store at 4° C.
16. Mouse Anti-Human IL-2 Capture Antibody stock solution (480 µg/mL): Reconstitute each vial with 0.5 mL of PBS. Store at 4° C.
17. Biotinylated Goat Anti-Human IL-2 Detection Antibody stock (6.0 µg/mL): Reconstitute each vial with 1.0 mL of Reagent Diluent. Close the cap and gently flip over the vial to dissolve the protein. Store at 4° C.

IL-2 ELISA Procedures
1. Preparation of the capture antibody working solution (4 µg/ml): Into 16.0 ml PBS in a 50 ml screw-capped tube, 0.133 ml of Mouse Anti-Human IL-2 Capture Antibody stock solution (480 µg/ml) was added and vortexed to mix.
2. The plate was coated by adding 100 µl/well capture antibody working solution. The plate was covered with plastic film and incubated overnight at 4° C. (13:30-16:00 RT, then 16:00-8:30 next day at 4° C.).
3. The next morning, each well was aspirated and washed by filling each well with 300 µl Wash Buffer. The process was repeated two times for a total of three washes. Removal of liquid at each step was complete for good performance After the last wash, any remaining Wash Buffer was removed by aspirating.
4. Plates were blocked by adding 200 µL/well of Block Buffer to each well. Plates were incubated at room temperature for 2 hours with gentle shaking (~100 rpm) (8:50-11:00).
5. The aspiration/wash was repeated as in step 3 to prepare the plates for sample addition.
6. During blocking, the IL-2 working standard solution was prepared for a 7-point standard curve by a 2-fold serial dilution into the Reagent Diluent with the first standard concentration of 1000 µg/ml in a 1.0 ml Eppendorf tube. To make the 1000 µg/ml standard, 16.7 µL 60 ng/mL standard was diluted to 1.50 mL Reagent diluent buffer, and vortexed. Two sets were prepared for 2 plates.
7. Each sample was diluted in Reagent Diluent accordingly.
8. 100 µL/well of each standard and sample working solution was pipetted to the wells according to the plate layout.
9. The plate was covered with plastic film, and incubated at RT for 1.5 hours with gentle shaking (~100 rpm) (11:30-13:00).
10. The aspiration/wash was repeated as in step 3.
11. Preparation of the detection antibody working solution (100 ng/ml): Into 16.0 ml Reagent Diluent in a 50 ml screw-capped tube, 0.266 ml of Biotinylated Goat Anti-Human IL-2 Detection Antibody stock solution and 320 µl normal goat serum were added and vortexed to mix.
12. 100 µL/well of the Detection Antibody working solution was added; the plate was covered with plastic film and incubated at RT for 1.5 hours with gentle shaking (~100 rpm).
13. The aspiration/wash was repeated as in step 3.
14. Preparation of the Streptavidin-HRP working solution (40× dilution): Into 16.0 ml Reagent Diluent in a 50 ml screw-capped tube, 0.400 ml of Streptavidin-HRP stock solution was added and vortexed to mix.
15. 100 µL of the working dilution of Streptavidin-HRP was added to each well. The plate was covered and incubated for 20 minutes at room temperature with gentle shaking (~100 rpm).
16. The aspiration/wash was repeated as in step 3.
17. Preparation of substrate working solution: 18.0 ml acetate-citrate (100 mM, pH 4.5) buffer, 2.0 ml DMSO, and 0.200 mL TMB, and 40.0 µl $H_2O_2$ (30%) were mixed and direct light on the plate was avoided.
18. 100 µL of Substrate Solution was added to each well and incubated for 30 minutes at room temperature with shaking (~200 rpm). The time depended on color developed, usually between 10 to 60 min. The OD was checked before adding Stop solution. Direct light on the plate was avoided.
19. 100 µL of Stop Solution was added to each well. The plate was gently tapped to ensure thorough mixing.
20. The optical density of each well was determined immediately, using a microplate reader set to 450 nm for signal OD and to 570 nm for background OD. Readings at 570 nm were subtracted from the readings at 450 nm.

Results

Figure 2:
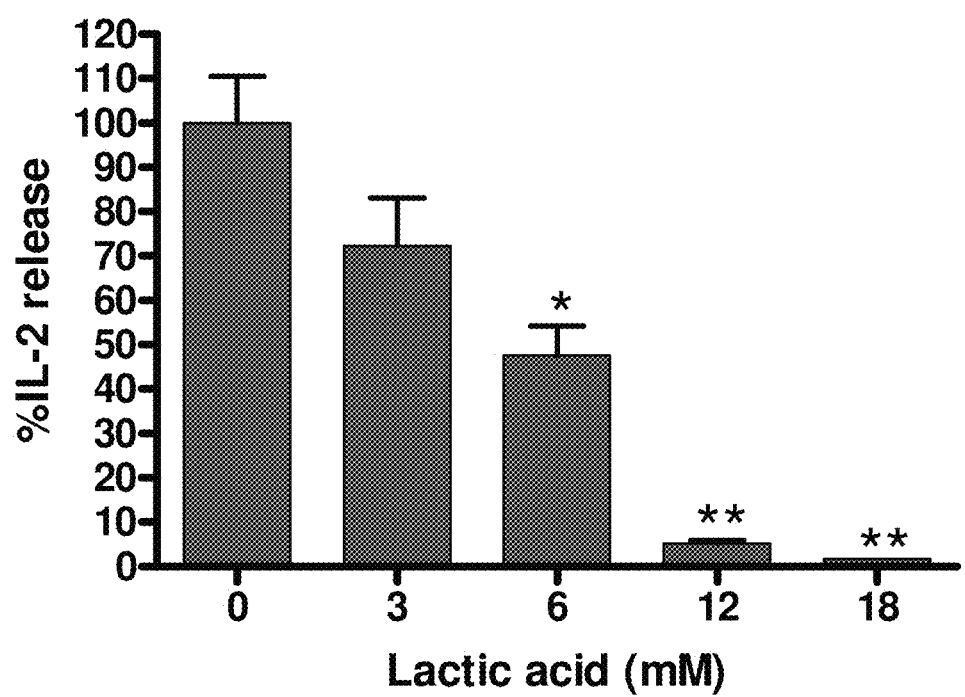
FIG. 2. Effects of lactic acid on IL-2 release in activated Jurkat cells. Jurkat cells ($5 \times 10^6$ cells/mL) were activated by incubation in complete RPMI medium containing 2.5 μg/mL PHA, 50 ng/mL PMA, and 0.75 μg/mL Ionomycin at 37° C. for 24 hours. IL-2 released by the activated Jurkat cells was measured using a sandwich ELISA. It was found that lactic acid at concentrations >6 mM caused a significant decrease in IL-2 production (* $p<0.05$ and ** $p<0.01$ as compared to the control).

Jurkat cells ($5 \times 10^6$ cells/mL) were activated by incubation in complete RPMI medium containing 2.5 µg/mL PHA, 50 ng/mL PMA, and 0.75 µg/mL Ionomycin at 37° C. for 24 hours. IL-2 released by the activated Jurkat cells was measured using a sandwich ELISA. As shown in FIG. 2, it was found that lactic acid at concentrations ≥6 mM caused a significant decrease in IL-2 production (* $p<0.05$ and ** $p<0.01$ as compared to the control).

Example 3—Protective Effects of L-DOS47/Urea on Jurkat Cells Cultivated in Lactic Acid-Treated Medium Materials
1. Advanced RPMI-1640 medium containing 5% FBS, Glutamax, and antibiotics
2. Lactic acid, 6.03 M
3. L-DOS47 (2128-101, 1.89 mg/mL)
4. Urea, 2.6 M 5. PBS, 10 mM, pH 7.4
6. Trypan blue solution, 0.4% (w/v) in PBS Procedures 1. Jurkat cells were prepared at $3 \times 10^6$ cells/mL in complete culture media;
2. 1.0 mL/well of cell culture was into a 24-well culture plate;
3. The plate was incubated at 37° C. overnight;
4. The next morning, L-DOS47 was prepared at 42 µg/mL and 25 µL/well was added to corresponding wells to a final concentration of 1 µg/mL;
5. Then, urea was prepared at 168 mM and 25 µL/well was added to corresponding wells to a final concentration of 4 mM;
6. the contents of the wells were mixed by gently swirling the plate;
7. Lactic acid was added to corresponding wells to a final concentrations of 6, 12, or 18 mM;
8. The contents of the wells were mixed by gently swirling the plate;
9. The plate was incubated at 37° C. and 5% $CO_2$ overnight;
10. 60 µL cell culture was taken from each well and 20 µL of Trypan blue solution was added to perform cell counts.

Results

Figure 3:
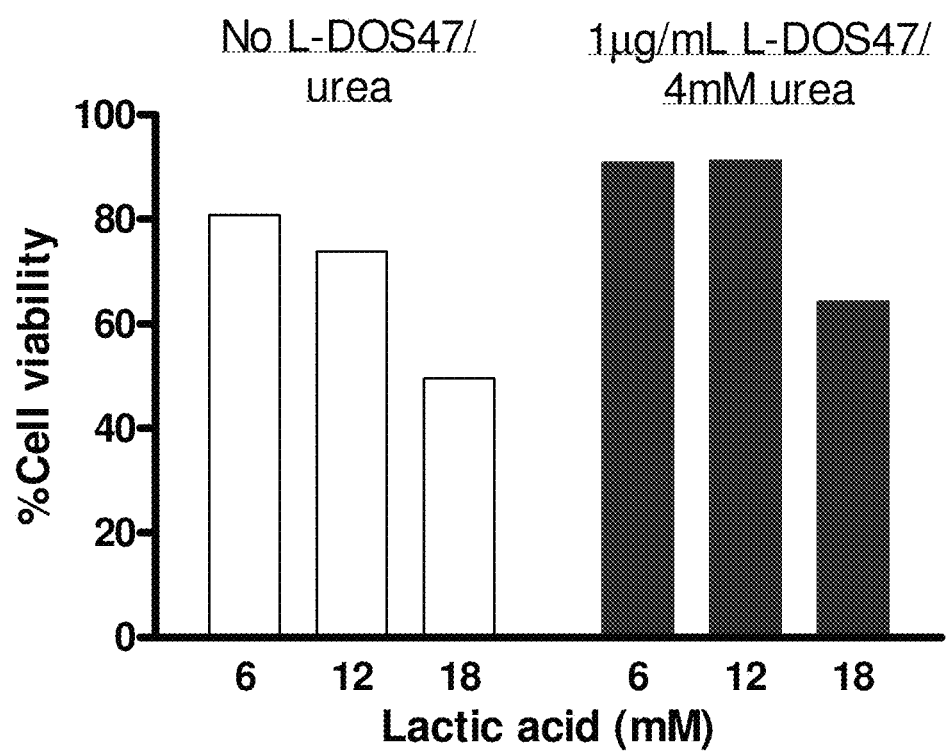
FIG. 3. Protective effects of L-DOS47/urea on Jurkat cells cultivated in lactic acid-treated medium. Jurkat cells ($3 \times 10^6$ cells/mL) were incubated in complete RPMI 1640 medium containing 6 to 18 mM of lactic acid for 1 day. Cell count was performed using a hemocytometer after Trypan Blue staining. Cell proliferation was found to be reduced by 20% to 50% (open bars). Addition of L-DOS47 (1 μg/mL) and urea (4 mM) suppressed the growth inhibitory effects of lactic acid and increased cell viability (solid bars).

Jurkat cells ($3 \times 10^6$ cells/mL) were incubated in complete RPMI 1640 medium containing 6 to 18 mM of lactic acid for 1 day. Cell count was performed using a hemocytometer after Trypan Blue staining. As shown in FIG. 3, cell proliferation was found to be reduced by 20% to 50% (open bars). Addition of L-DOS47 (1 µg/mL) and urea (4 mM) suppressed the growth inhibitory effects of lactic acid and increased cell viability (solid bars).

Example 4—Restoration of IL-2 Production in Lactic Acid-Treated Jurkat Cells

Materials

1. Advanced RPMI-1640 medium containing 5% HIFBS, Glutamax, and antibiotics
2. Cell stimulation reagents:
   Phorbol 12-myristate 13-acetate (PMA), 5 µg/mL, Abcam cat # AB120297
   Phytohemagglutinin (PHA), 2 mg/mL, Sigma cat # L8754)
3. Lactic acid, 6.03 M
4. L-DOS47 (2128-101, 1.89 mg/mL)
5. Urea, 2.6 M
6. Trypan blue solution, 0.4% (w/v) in PBS Procedures 1. Jurkat cells at $4 \times 10^6$ cells/mL in HIFBS medium were prepared;
2. 0.5 mL/well of cell culture was added into two 24-well culture plates;
3. Plates were incubated at 37° C. and 5% $CO_2$ overnight;
4. In the next morning, L-DOS47 was prepared at 15 µg/mL and 40 µL/well was added to corresponding wells to a final concentration of 1 µg/mL;
5. Then, urea was prepared at 60 mM, and 40 µL/well was added to corresponding wells to a final concentration of 4 mM;
6. The contents of the wells were mixed by gently swirling the plate;
7. Lactic acid was added to corresponding wells at 1.2 or 2.4 µL/well to a final concentrations of either 6 or 12 mM;
8. The contents of the wells were mixed by gently swirling the plate;
9. A mixture of PHA and PMA at 60 and 1.5 µg/mL, respectively, was prepared and 20 µL/well of the solution was added to corresponding wells to a final concentration of 2.0 µg/mL and 50 ng/mL, respectively;
10. Plates were incubated at 37° C. and 5% $CO_2$ for 24 hrs;
11. Cell culture from each well was transferred to Eppendorf tubes and centrifuged at 7000 rpm for 10 min to collect supernatant;
12. An ELISA was performed to determine the amount of IL-2 released by Jurkat cells.

Results

Figure 4:
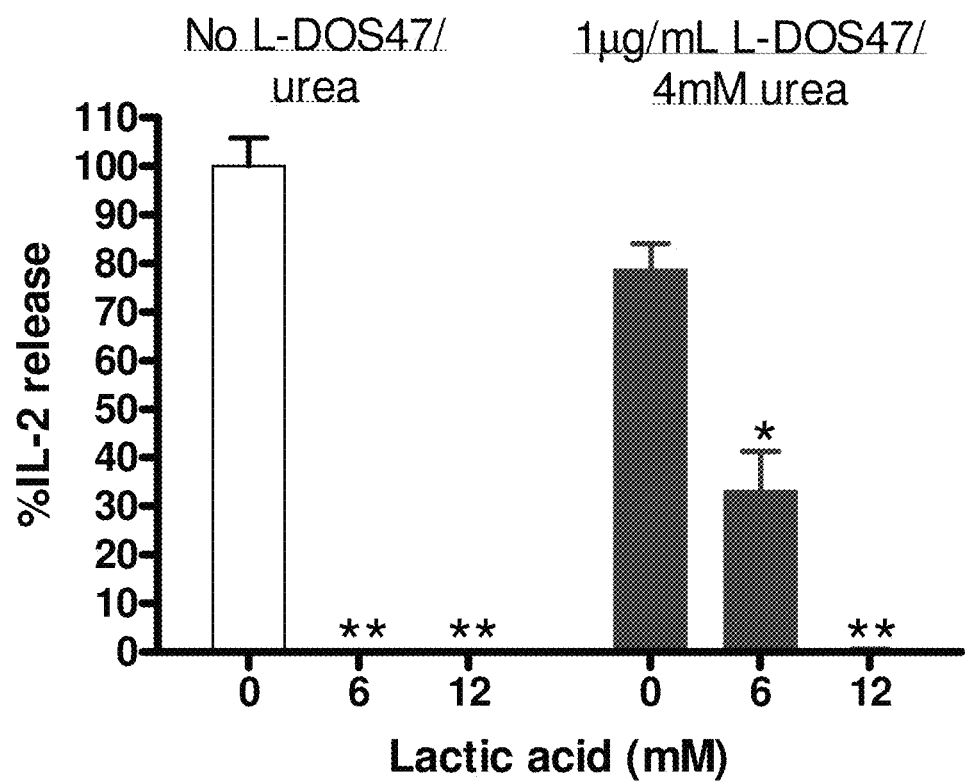
FIG. 4. Restoration of IL-2 production in lactic acid-treated Jurkat cells. Lactic acid inhibited IL-2 production in Jurkat cells stimulated with 2 μg/mL PHA and 50 ng/mL PMA, which was partially restored by addition of 1 μg/mL L-DOS47 and 4 mM urea in medium containing 6 mM lactic acid. At higher acid concentration (12 mM), the tested L-DOS47 and urea combination are insufficient to restore IL-2 release. Where * $p<0.05$ and ** $p<0.005$ as compared to the blank medium.

Lactic acid inhibited IL-2 production in Jurkat cells stimulated with 2 µg/mL PHA and 50 ng/mL PMA, which was partially restored by addition of 1 µg/mL L-DOS47 and 4 mM urea in medium containing 6 mM lactic acid (FIG. 4). At higher acid concentration (12 mM), the tested L-DOS47 and urea combination are insufficient to restore IL-2 release. Interestingly, in native medium with no lactic acid, addition of L-DOS47/urea seems to reduce IL-2 production by about 20%, which is however not quite statistically significant (p=0.0622). Where * $p<0.05$ and ** $p<0.005$ as compared to the blank medium.

Example 5—Restoration of PD-1 Expression in Lactic Acid-Treated Jurkat Cells

Materials

1. Advanced RPMI-1640 medium containing 5% HIFBS, Glutamax, and antibiotics
2. Anti-CD3 antibody, 1 mg/mL
3. Anti-CD28 antibody, 0.5 mg/mL
4. Lactic acid, 6.03 M
5. L-DOS47 (2128-101, 1.89 mg/mL)
6 Urea, 2.6 M
7. Trypan blue solution, 0.4% in PBS
8. Trustain fcx, BioLegend 422301
9. Biotin-anti-PD-1 Ab, 0.5 mg/mL, Biolegend 329934
10. Streptavidin-AP, 1 mg/mL
11. 4-nitrophenyl phosphate disodium salt hexahydrate, Fluka (use: 1 mg/ml)
12. Diethanolamine substrate buffer, 5× concentrate
13. Buffer A, 0.05% BSA/PBS
14. Paraformaldehyde, 20%
15. PBS, 10 mM, pH 7.4
16. 5% BSA in PBS
17. TBS-T: TBS containing 0.05% Tween-20
18. Buffer B: PBS containing 0.05% BSA and 0.05% Tween-20

Procedures

1. A 12-well plate was coated with 0.5 mL/well of anti-CD3 antibody (10 µg/mL in PBS) and incubated at 37° C. for 1 hr;
2. Plate was washed 1× with 2 mL PBS;
3. Jurkat cells were prepared at $5 \times 10^6$ cells/mL in media containing 2 µg/mL anti-CD28 antibody;
4. L-DOS47/urea solution in media was prepared (4 µg/mL, and 0, 8, 16 mM);
5. Lactic acid solution in media was prepared (0, 24, 48 mM);
6. 1 mL/well of cell mixture, 0.5 mL/well L-DOS47 solution (final concentration 1 µg/mL L-DOS47 with 2 or 4 mM urea), and 0.5 mL/well LA solution (final concentration 6 and 12 mM) was added to corresponding wells;
7. Plate was incubated at 37° C. and 5% $CO_2$ for 3 days;
8. 80 µL of cell culture was taken from each well and for a cell count by adding 20 µL of Trypan blue solution;

9. Cell density was adjusted to 8×10⁶/mL in PBS and 100 µL/well of the cell samples was added to a 96-well plate in triplicate;

10. Plate was centrifuged at 400 g for 5 min;

11. Cells were fixed by slowly adding 100 µL/well of 3% paraformaldehyde/PBS and incubate at RT for 15 min;

12. Plates were washed 2× with PBS;

13. Plate was blocked with 200 µL/well of 3% BSA at 4° C. o/n;

14. Plates were washed 1× with TBS-T;

15. Fc binding was blocked by adding Trustain fcx (50 µL/mL, 100 µL/well) for 30 min at 4° C.;

16. Plates were washed 2× with TBS-T;

17. 100 µL/well of Biotin-anti-PD-1 Ab (1:1000 in Buffer B) was added;

18. Plates were incubated at RT for 1.5 hr with gentle shaking;

19. Plates were washed 3× with TBS-T;

20. 100 µl/well anti-mouse-IgG-AP (1:5000 in Buffer B) was added;

21. Plates were incubated at RT for 1 hr with gentle shaking;

22. Plates were washed 3× with TBS-T;

23. 100 µl/well AP substrate was prepared at 1 mg/ml in diethanolamine buffer and added and incubated for 1 hour at RT with shaking;

24. $OD_{405}$ was read with microplate reader.

Results

Figure 5:
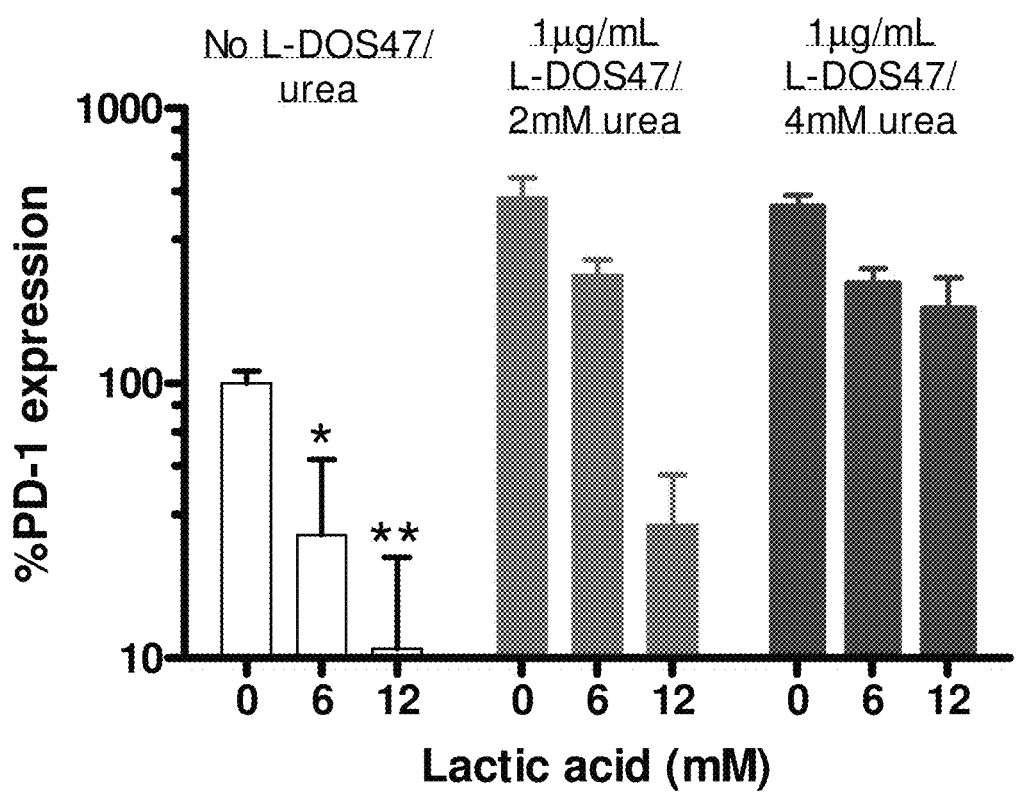
FIG. 5. Restoration of PD-1 expression in lactic acid-treated Jurkat cells. Expression of PD-1 on Jurkat cells was evaluated by whole-cell ELISA. The cells were stimulated to express PD-1 receptor by immobilized anti-CD3 antibody and soluble anti-CD28 antibody (data not shown). Addition of lactic acid significantly reduced PD-1 expression (open bars, * p<0.05 and ** p<0.005), while addition of L-DOS47/urea greatly enhanced PD-1 expression (solid bars).

Expression of PD-1 on Jurkat cells was evaluated by whole-cell ELISA. The cells were stimulated to express PD-1 receptor by immolized anti-CD3 antibody and soluble anti-CD28 antibody (data not shown). FIG. 5 shows that addition of lactic acid significantly reduced PD-1 expression (open bars, * $p<0.05$ and ** $p<0.005$), while addition of L-DOS47/urea greatly enhanced PD-1 expression (solid bars).

Example 6—Interferon Gamma-Stimulated Tumors and their Effects on IL-2 Release from Activated Jurkat Cells Materials 1. Advanced RPMI-1640 medium containing 5% HIFBS, Glutamax, and antibiotics 2. Interferon gamma, 0.1 mg/mL 3. PBS, 10 mM, pH 7.4

4. Cell stimulation reagents:
Phorbol 12-myristate 13-acetate (PMA), 5 µg/mL, Abcam cat # AB120297
Phytohemagglutinin (PHA), 2 mg/mL, Sigma cat # L8754)

Procedures

1. BxPC-3 and MDA-MB231 cells were prepared at 2×10⁵ cells/mL in complete culture media;

2. 400 µL/well of cell culture was seeded into a 24-well culture plate containing 200 µL/well of culture media;

3. IFNγ was prepared from 12 to 0.75 ng/mL at ¼× dilution and 120 µL/well was added to corresponding wells to a final concentration of 2 to 0.125 ng/mL;

4. Plates were swirled gently to mix the contents in the wells;

5. Plates were incubated at 37° C. for 2 days;

6. Jurkat cells were prepared at 4×10⁶ cells/mL in HIFBS media;

7. Wells were emptied and 0.5 mL/well Jurkat cells were added;

8. A mixture of PHA and PMA at 22 and 0.55 µg/mL, respectively, was prepared and 50 µL/well of the solution was added to corresponding wells to a final concentration of 2.0 µg/mL and 50 ng/mL, respectively;

9. IFNγ was prepared from 112 to 7 ng/mL at ¼× dilution and 10 µL/well was added to corresponding wells to a final concentration of 2 to 0.125 ng/mL;

10. Plates were incubated at 37° C. for 24 hrs;

11. In the next morning, cell culture was transferred from each well to Eppendorf tubes and centrifuged at 7000 rpm for 10 min to collect supernatant;

12. An ELISA was performed to determine the amount of IL-2 released by Jurkat cells.

Results

Figure 6:
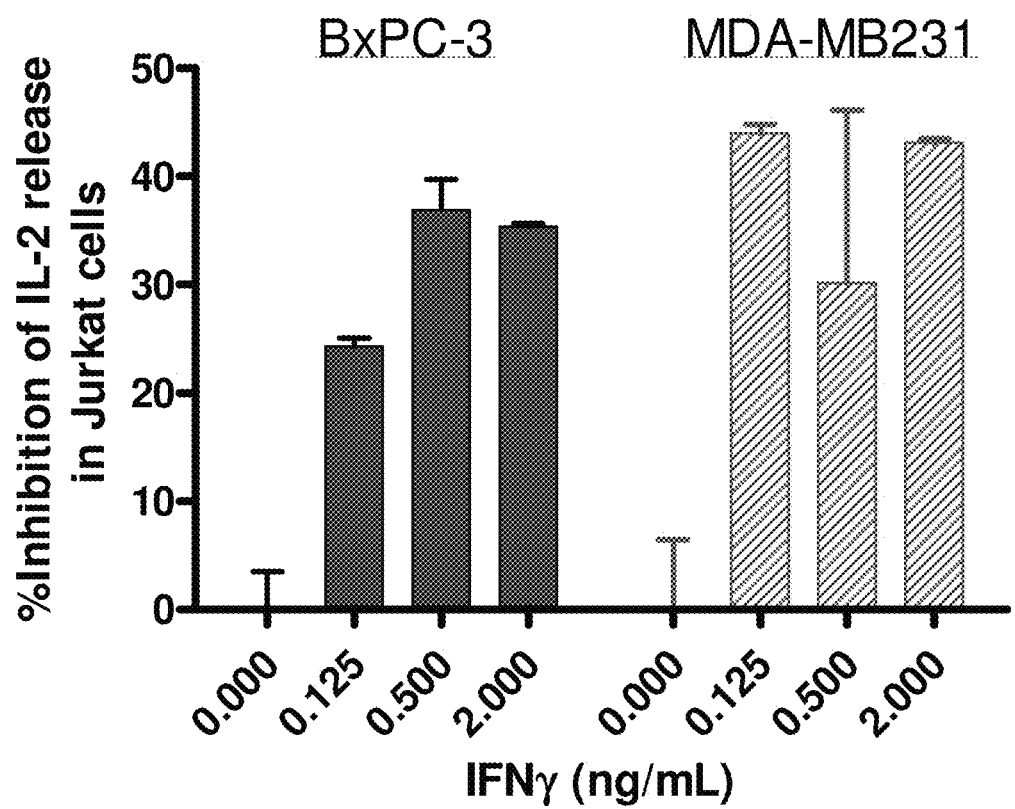
FIG. 6. Interferon gamma-stimulated tumors and their effects on IL-2 release from activated Jurkat cells. BxPC-3 and MDA-MB231 tumor cells were stimulated with various concentrations of IFNγ for 2 days. After removal of the original media, activated Jurkat cells were added and co-cultured with the tumor cells for 24 hours at 37° C. The results show that IFNγ stimulated tumor cells inhibit IL-2 release in Jurkat cells by as much as 40%.
Figure 7A:
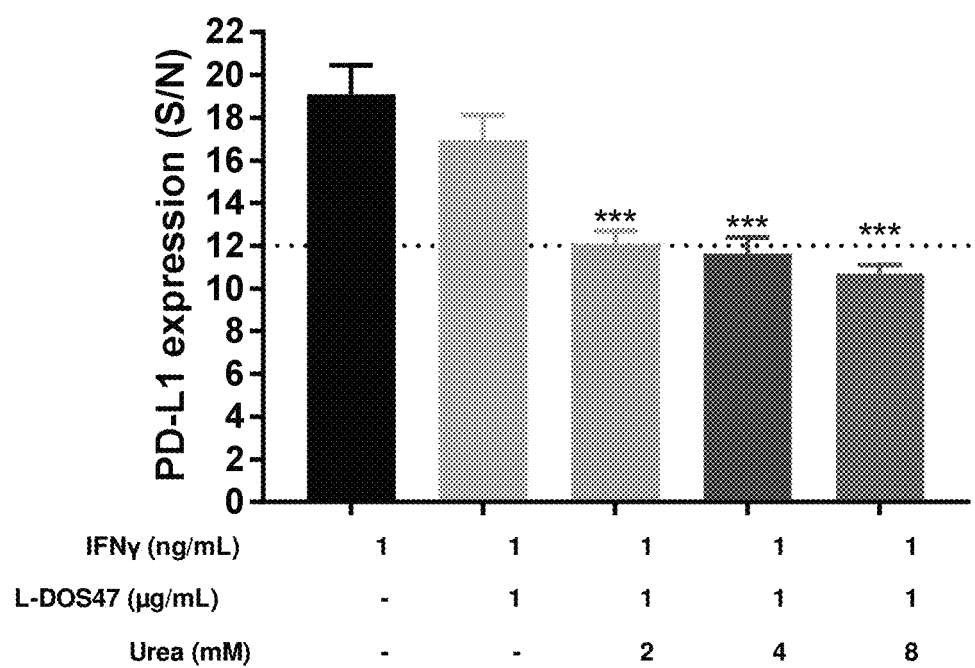
FIGS. 7A-B. L-DOS47+ urea treatment reduces PD-L1 expression on IFNγ-stimulated MDA-MB-231 breast cancer cells.
Figure 7B:
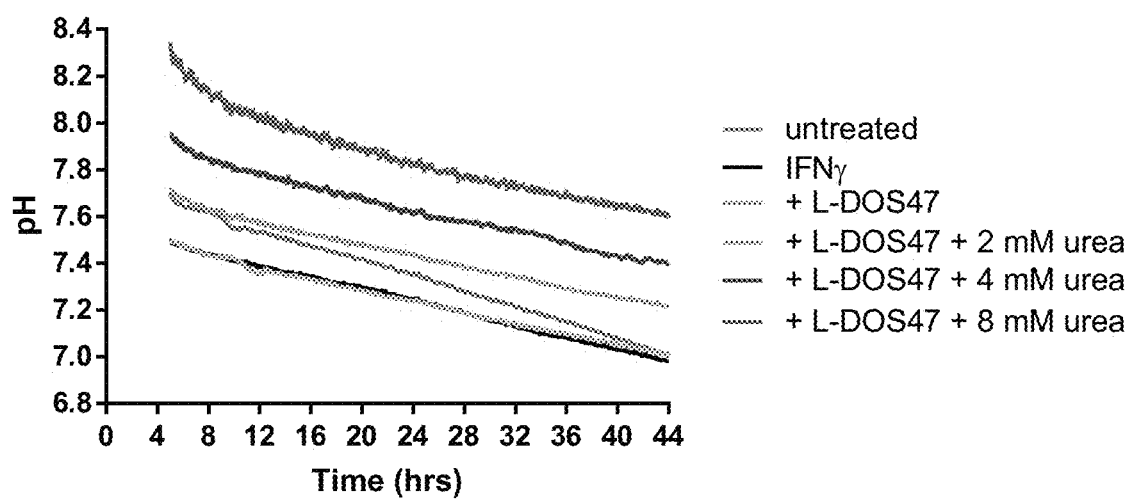
Figure 8A:
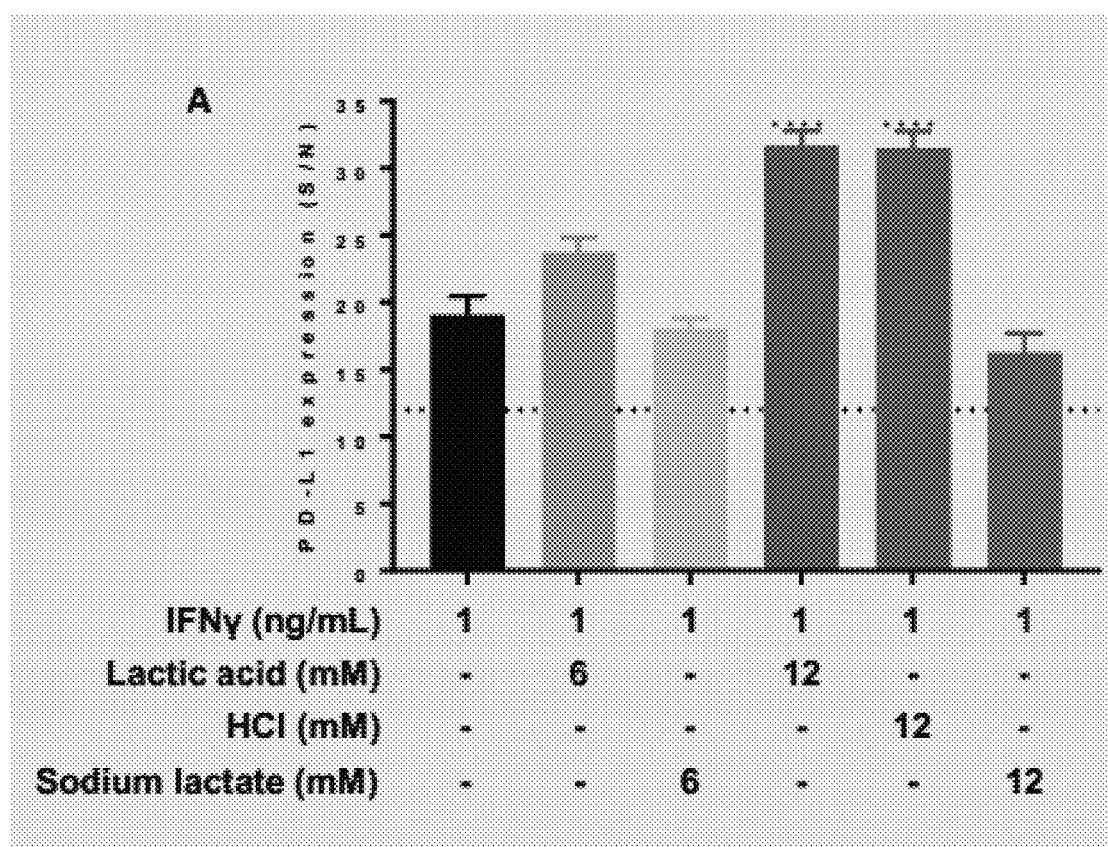
FIGS. 8A-B. Lactic acid treatment increases PD-L1 expression on IFNγ-stimulated MDA-MB-231 breast cancer cells.
Figure 8B:
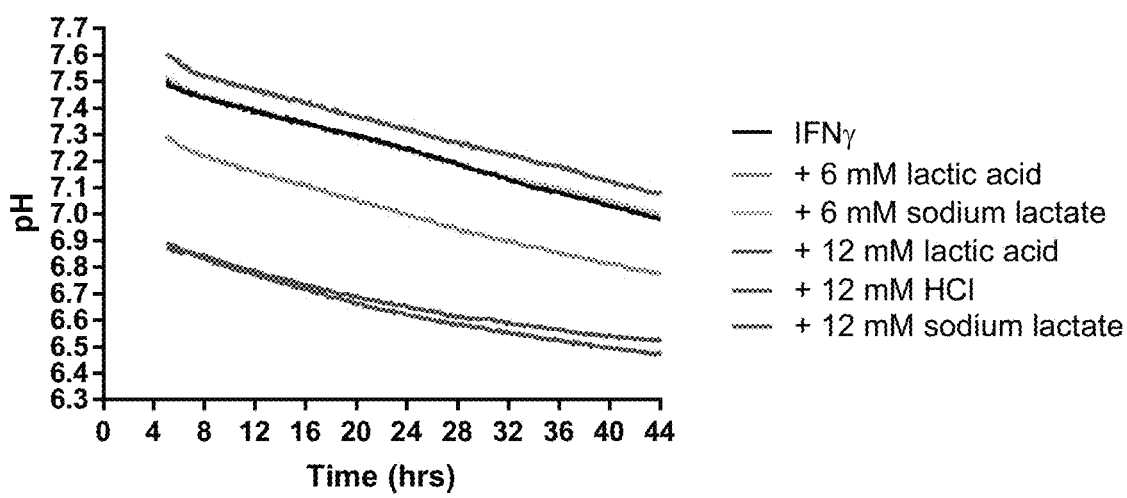
Figure 9A:
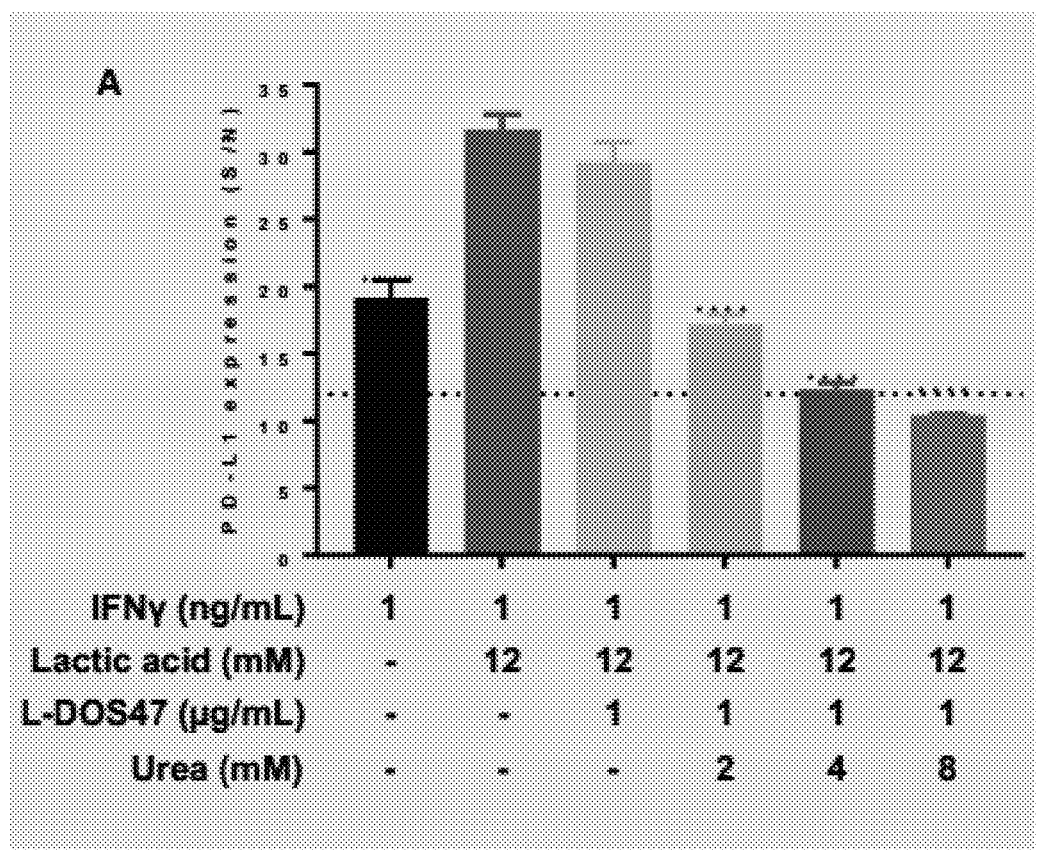
FIGS. 9A-B. L-DOS47+ urea treatment restores low PD-L1 expression on lactic acid and IFNγ-treated MDA-MB-231 breast cancer cells.
Figure 9B:
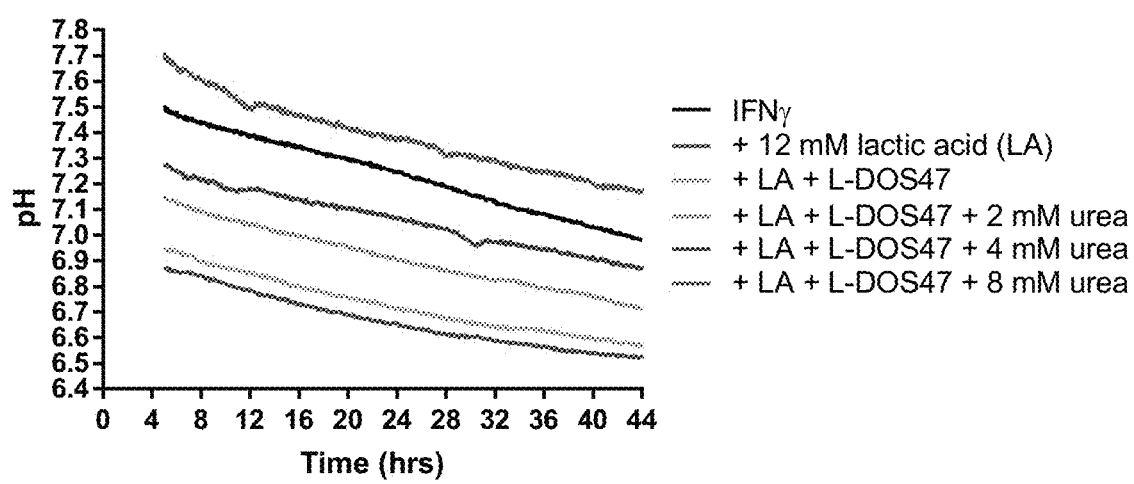
Figure 10A:
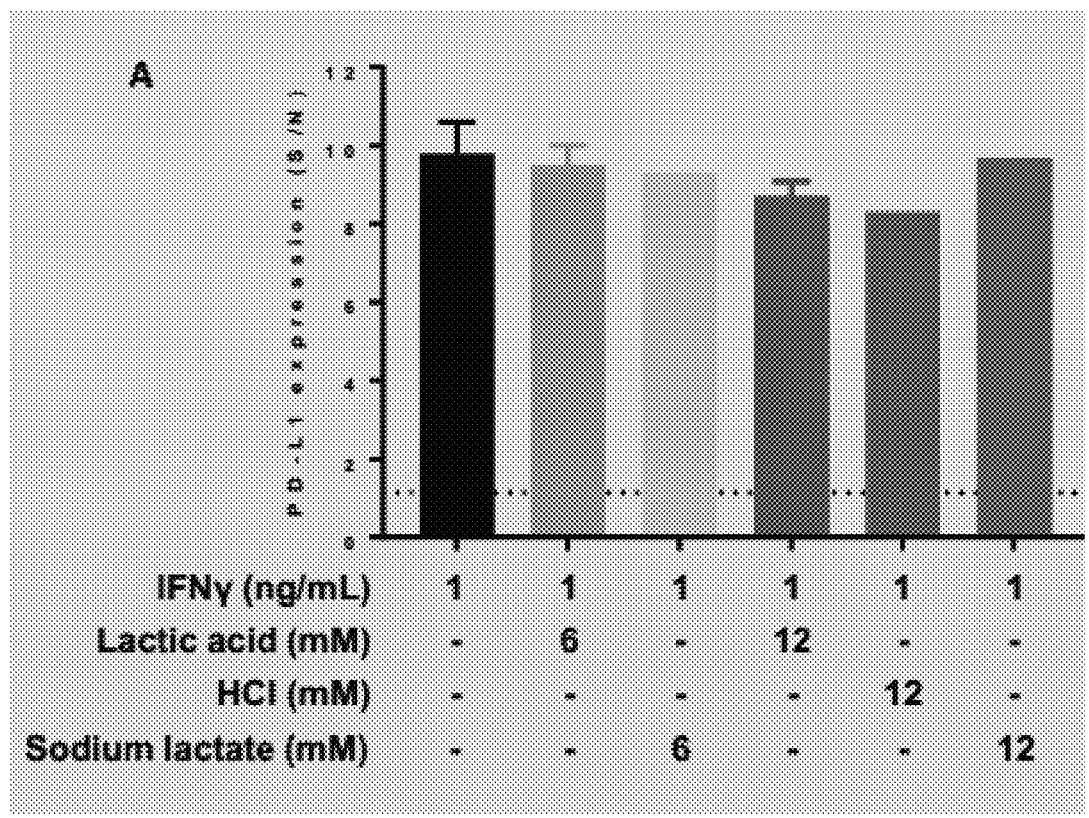
FIGS. 10A-B Lactic acid treatment has no effect on PD-L1 expression on IFNγ-stimulated SKOV-3 ovarian cancer cells.
Figure 10B:
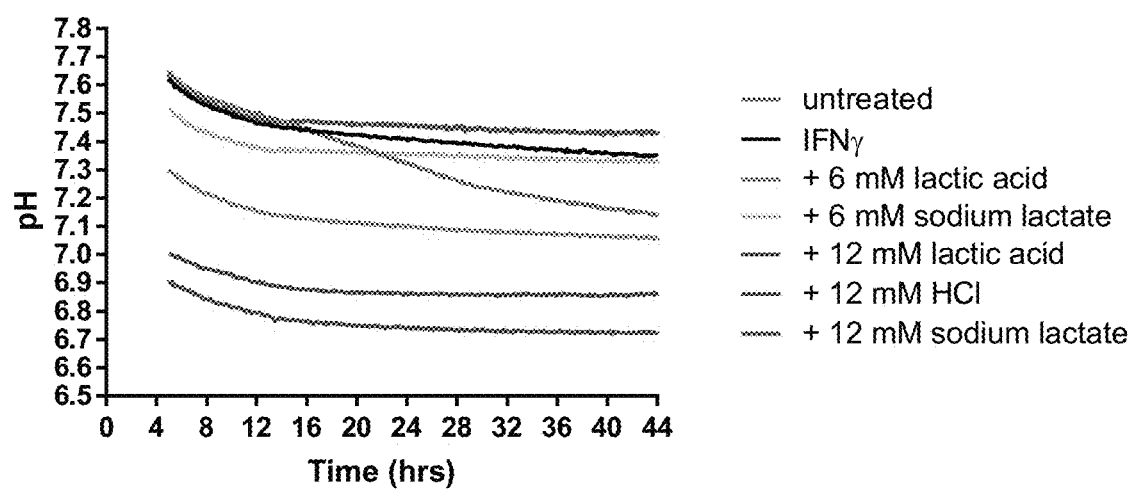
Figure 11A:
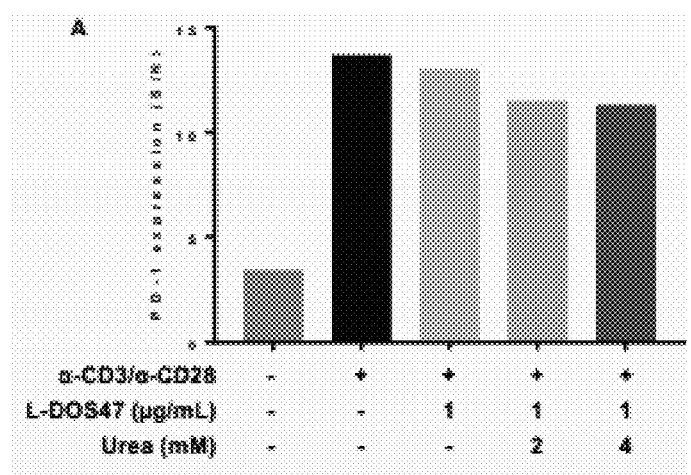
FIGS. 11A-D. L-DOS47+ urea treatment increases IL-2 and IFNγ production by activated CD8+ T cells. CD8+ T cells were purified from donor PBMC using negative selection methods. Cells were activated with α-CD3/α-CD28 Dynabeads® and IL-2 for 3 days before the initiation of the experiment.
Figure 11B:
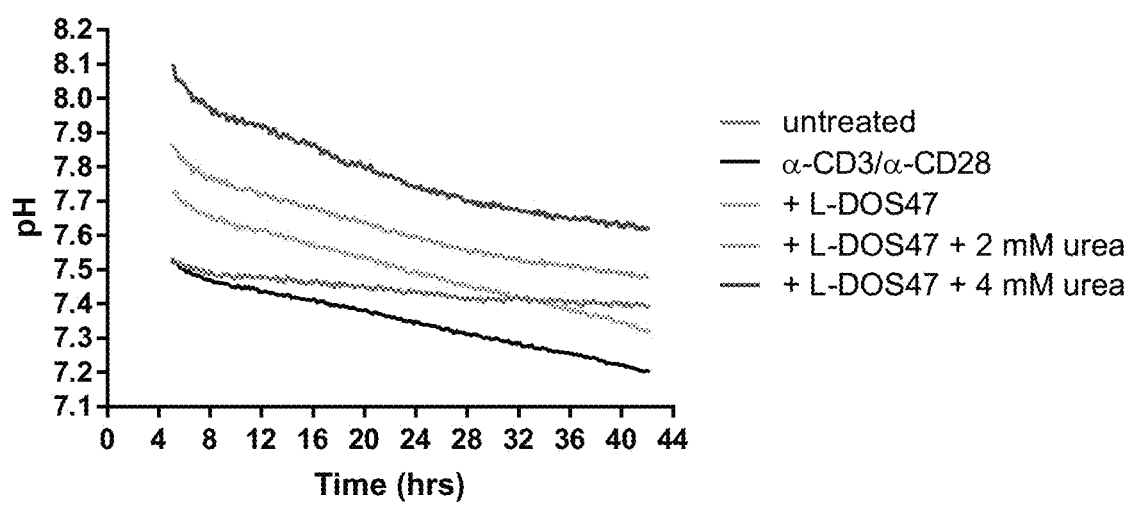
Figure 11C:
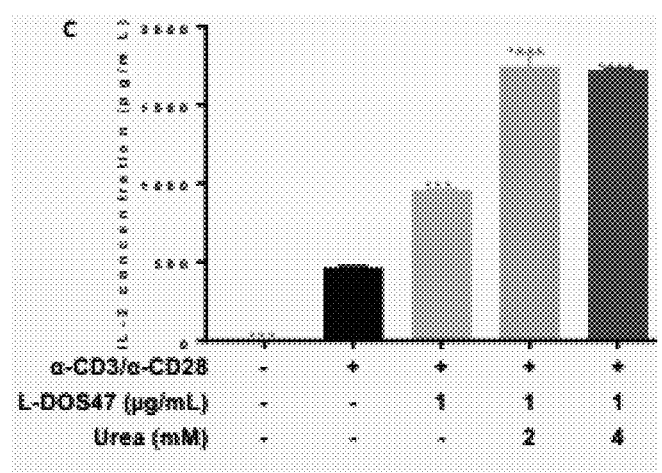
Figure 11D:
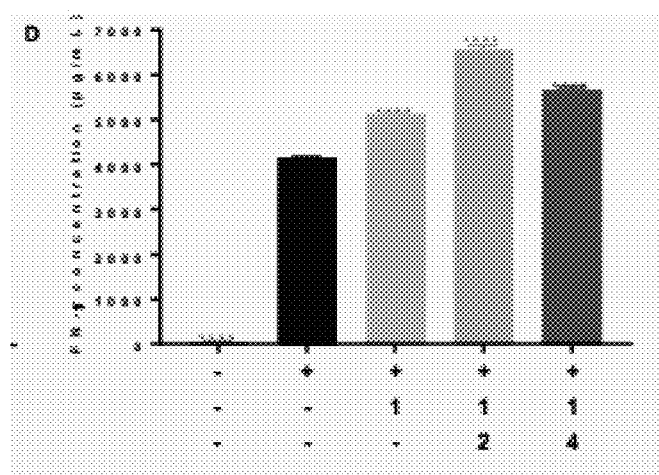
Figure 12A:
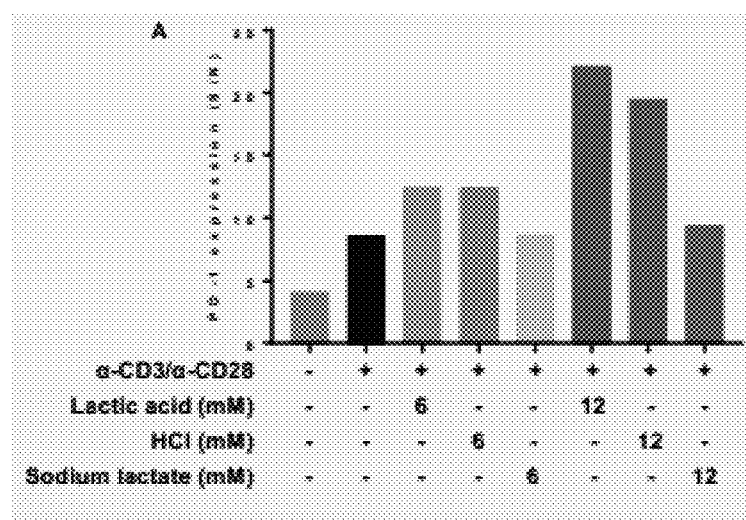
FIGS. 12A-D. Lactic acid increases PD-1 expression and decreases IFNγ production by activated CD8+ T cells.
Figure 12B:
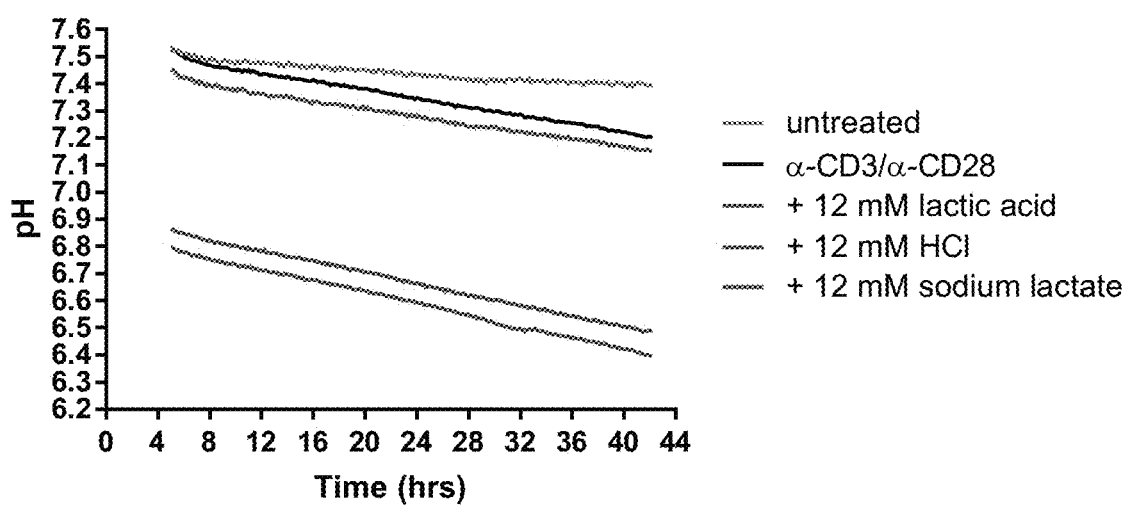
Figure 12C:
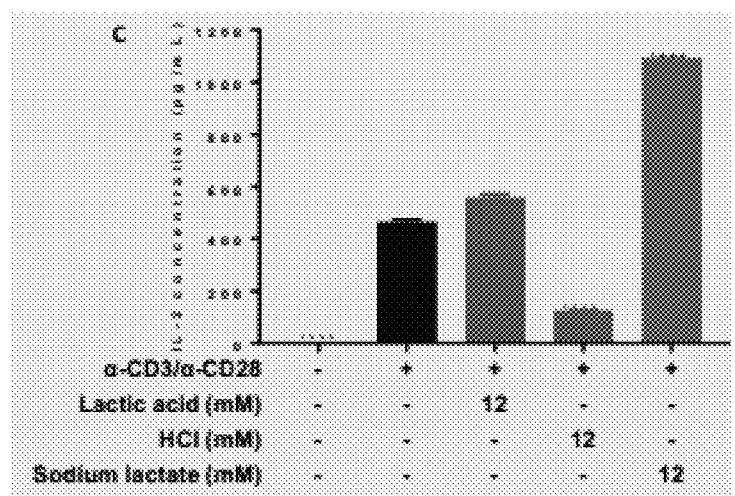
Figure 12D:
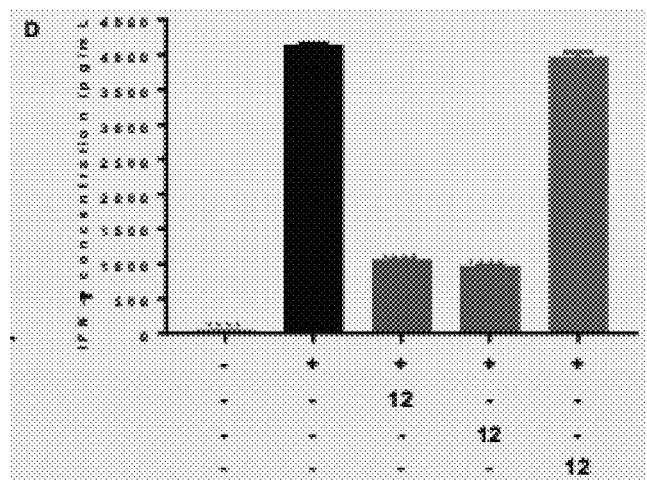
Figure 13A:
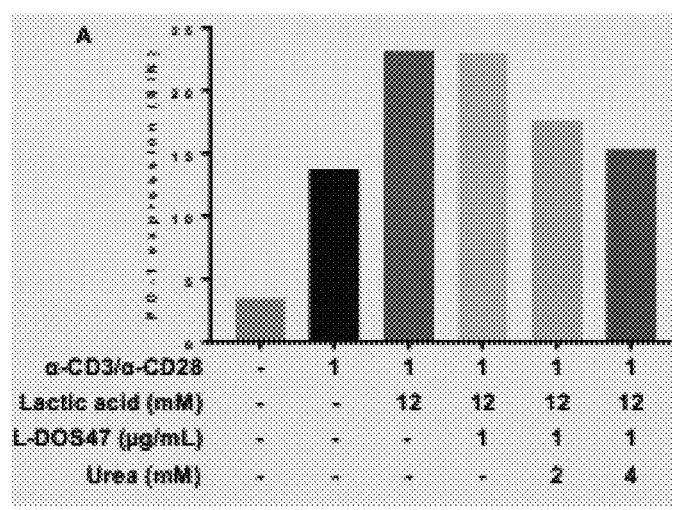
FIGS. 13A-D. L-DOS47+ urea treatment of lactic acid-cultured, activated CD8+ T cells reduces PD-1 expression, increases IL-2 production and restores high IFNγ production.
Figure 13B:
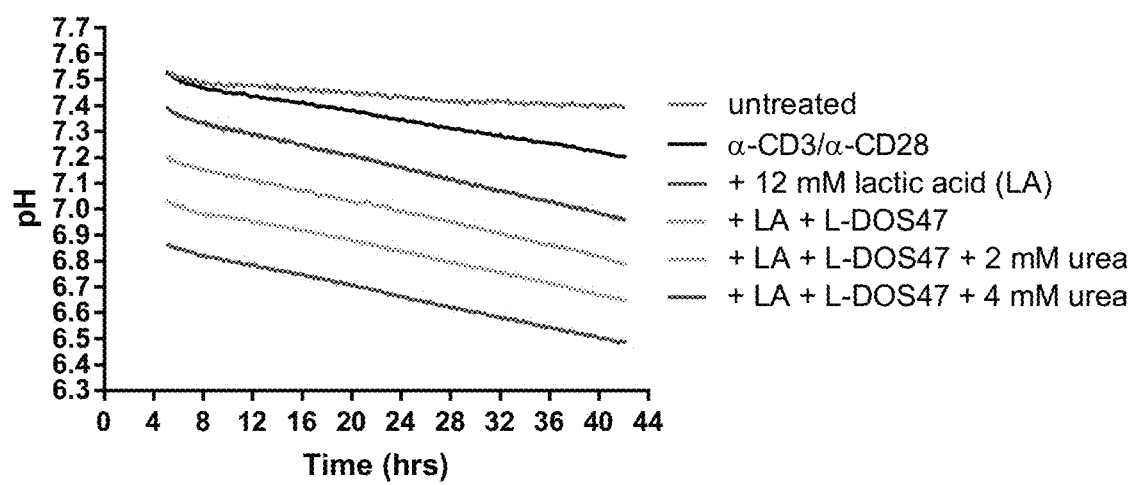
Figure 13C:
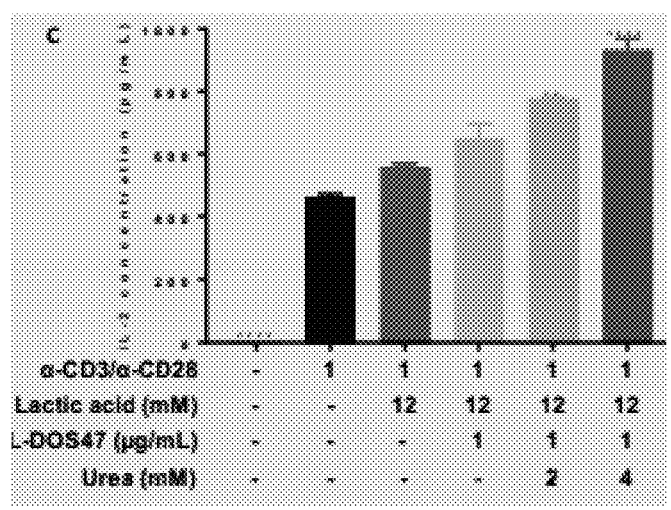
Figure 13D:
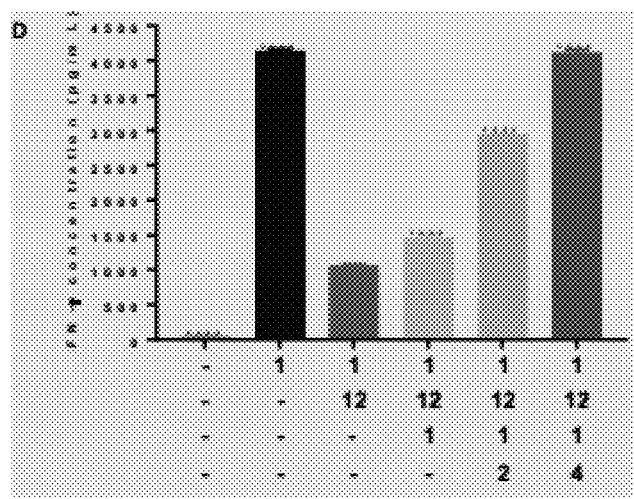

BxPC-3 and MDA-MB231 tumor cells were stimulated with various concentrations of IFNγ for 2 days. After removal of the original media, activated Jurkat cells were added and co-cultured with the tumor cells for 24 hours at 37° C. The results in FIG. 6 show that IFNγ stimulated tumor cells inhibited IL-2 release in Jurkat cells by as much as 40%.

Example 7—Examining the Effects of Lactic Acid, HCl, Sodium Lactate and/or L-DOS47+/− Urea on PD-L1 Expression by MDA-MB-231 and SKOV-3 Cells (Shown in FIGS. 7-10)

Materials

1. Advanced RPMI-1640 medium containing 5% HIFBS, Glutamax, and antibiotics

2. Lactic acid, 6.03N

3. L-DOS47 (2128-101, 1.89 mg/mL)

4 Urea, 2.6 M

5. Sodium lactate, 3 M in PBS

6. Biotin-anti-PD-L1 Ab, 0.5 mg/mL, Biolegend

7. PE-Streptavidin, 0.2 mg/mL, Biolegend 405204

8. Paraformaldehyde, 20%

9. DPBS (1.47 mM $KH_2PO_4$, 8.06 mM $Na_2HPO_4$, 2.67 mM KCl, and 138 mM NaCl, 0.5 mM EDTA, pH 7.4)

10. FACS staining buffer: (DPBS containing 0.02% $NaN_3$ and 0.1% BSA)

11. 12×75 mL polystyrene tubes

12. Non-enzymatic cell dissociation solution

13. Interferon gamma, 0.1 mg/mL

14. HCl

15. BSA, 5%

16. Hydrodish HD24—24-well plate with integrated pH sensors

Procedures

1. MDA-MB231 or SKOV-3 cells were prepared at 2×10⁵ cells/mL in complete culture media 2. Cell culture was seeded into a 24-well Hydrodish plate and incubated at 37° C. for 2 days 3. Media was removed and a 0.6 mL/well HIFBS media was added 4. IFNγ was prepared at 10 ng/mL and 100 µL/well was added to corresponding wells to a final concentration of 1 ng/mL 5. Plates were swirled gently to mix the contents in the wells 6. L-DOS47 was prepared at 10 µg/mL and 100 µL/well was added to corresponding wells to a final concentration of 1 µg/mL 7. Urea was prepared at 20, 40, and 80 mM and 100 µL/well was added to corresponding wells to a final concentration of 2, 4, and 8 mM 8. Lactic acid, HCl, or sodium lactate was prepared at 60 and 120 mM, and 100 μL/well was added to corresponding wells to a final concentration of 6 and 12 mM, respectively 9. Plates were swirled gently to mix the contents in the wells 10. The 24-well plate was placed on the SDR inside the incubator at 37° C. and 5% $CO_2$ for 2 days; pH change was monitored 11. Medium was removed from each well 12. Well were rinsed with 1 mL DPBS 13. Cells were detached with 0.3 mL/well non-enzymatic cell dissociation solution at RT for 10 mM (If cell clusters were observed, the sample was syringed through an 18 gauge needle by 3-5 passages to dissociate cell clusters)

14. The sample was transferred from each well to a centrifuge tube containing 0.3 mL FACS staining buffer 15. The cells were mixed and spun down at 300×g for 5 min 16. Cells were resuspended in 0.5 mL FACS staining buffer 17. Cell counts were performed on 20 μL of cell suspension 18. Cell density was adjusted to ~1×10$^5$ cells/100 μL in FACS staining buffer and 120 μL/well was transferred to a round-bottom 96-well plate for staining 19. Plates were centrifuged at 300×g for 3 min, supernatant was discarded with multi-channel pipette 20. 50 μL/well of the biotin-anti-PD-L1 antibody (1:100 in FACS staining buffer) was added 21. Incubated on ice for 30 min 22. Plates were washed 3× with 100 μL/well FACS staining buffer by centrifugation at 300×g for 3 min each 23. 50 μL/well PE-Streptavidin (1:1500 in FACS staining buffer) was added 24. Plates were covered with tin foil and incubated on ice for 30 min 25. Plates were washed 3× as in step 22 above 26. Cells were fixed by resuspending cell pellet from the last wash in 100 μL/well of 1% paraformaldehyde in PBS 27. Plates were covered with tin foil and incubated on ice for 30 min 28. Plates were washed 2× as in step 22 above 29. Plates were covered with tin foil and store at 2-8° C.

30. Plates were analyzed with Guava flow cytometer and FCS Express Software

Example 8—Examining the Effects of Lactic Acid, HCl, Sodium Lactate and/or L-DOS47+/− Urea on PD-1 Expression by Activated CD8+ T Cells (Results Shown in FIGS. 11-13)

Preparation and Activation of CD8+ T Cells
Materials
1. Advanced RPMI-1640 medium containing 10% FBS, Glutamax, and antibiotics
2. EasySep Human CD8+ T cell enrichment kit (Stemcell, cat #19053)
3. Human Leukopak PBMC (Bioreclamation IVT, Lot # BRH1239929; 5.97×10$^7$ cells/vial)
4. Dynabeads Human T-activator CD3/CD28 (Life Technologies, Cat #11131D)
5. DPBS (1.47 mM $KH_2PO_4$, 8.06 mM $Na_2HPO_4$, 2.67 mM KCl, and 138 mM NaCl, 0.5 mM EDTA, pH 7.4)
6. EasySep Buffer—DPBS containing 2% FBS and 2 mM EDTA ($Ca^{2+}/Mg^{2+}$ free)
7. Human IL-2, 10$^6$ U/mL, 0.1 mg/mL, Cedarlane CL101-02

Procedures
(A) Preparation of PMBC cells:
1. PMBC tube was removed from liquid nitrogen and wiped with 70% alcohol
2. Pressure of tube was released by loosening the cap and was then retightened
3. Cells were quickly thawed at 37° C.
4. 1 mL prewarmed medium was added to cells and cell suspension was transferred to a 50 mL conicle tube
5. Cryovial was rinsed with 1 mL medium
6. ~10× of original vial volume of medium was added
7. Vial was centrifuged at 220 g at RT for 10 min
8. Supernatant was removed with pipette and a small amount was left behind
9. 15 mL of EasySep Buffer was slowly added to resuspend pellet
10. Vial was centrifuged at 220 g at RT for 10 min
11. Remove all but 2 mL of supernatant and resuspend cell pellet (B) Preparation of CD8+ T cells:
1. Cells were counted and resuspended at 5×10$^7$ cells/mL→(cell count=1.45×10$^8$/mL at 1.6 mL total vol) [Add 3 mL→5×10$^7$ cells/mL]
2. Cells were added to a 12 mL polystyrene tube (final vol=4.6 mL)
3. Enrichment cocktail was added at 50 μL/mL of sample (total vol added=230 μL)
4. Cells were mixed and incubated at RT for 10 min
5. Magnetic particles were vortexed for 30 sec
6. Magnetic particles were added at 150 μL/mL of sample (total vol added=690 μL)
7. Tube was incubated at RT for 5 min
8. Tube was placed into magnet and incubated at RT for 5 min
9. The enriched cell suspension was poured into a new tube
10. Cell counts were performed (=6.63×10$^6$ cells/mL, total=5.3 mL or 3.37×10$^7$ cells)

(C) T cell activation:
1. Dynabeads were vortexed for >30 sec
2. 660 μL of Dynabeads were transferred to a tube
3. An eq. vol of EasySep Buffer or at least 1 mL was added and mixed (Vortexed for 5 sec)
4. Tube was placed on magnet for 1 min and supernatant was discarded
5. The washed Dynabeads were resuspended in the same vol of culture media as initial vol (660 μL)
6. T cells were activated by mixing with the washed Dynabeads
7. 30 U/mL IL-2 was added for T cell expansion (Total vol=15 mL; 450 μL of IL-2 added)
8. Cells were incubated at 37° C. and 5% $CO_2$ Example 9—Examine the Effects of Lactic Acid, HCl, Sodium Lactate and/or L-DOS47+/− Urea on PD-1 Expression, IL-2 Production and IFNγ Production from CD8+ T Cells Materials
1. Advanced RPMI-1640 medium containing 10% HIFBS, Glutamax, and antibiotics
2. Anti-CD3 antibody, 1 mg/mL, Cedarlane #CLANT144-2
3. Anti-CD28 antibody, 0.5 mg/mL, BioLegend 302902
4. Lactic acid, 6.03N 5. Sodium lactate, 3 M in PBS
6. HCl, 6N
7. L-DOS47 (Lot #2128-101), 1.7 mg/mL
8. Urea, 2.6 M
9. Biotin-anti-PD-1 Ab, 0.5 mg/mL, Biolegend 329934
10. Biotin-mouse IgG1 isotype control, 0.1 mg/mL, Cedarlene Cat #CLCMG115
11. Biotin-L-DOS47, Lot #170803, 1.67 mg/mL
12. Biotin-HPU (urease), Lot #170803, 1.25 mg/mL
13. PE-Streptavidin, 0.2 mg/mL, Biolegend 405204
14. Paraformaldehyde, 20%
15. DPBS with $Ca^{2+}$ and $Mg^{2+}$ (10 mM PBS containing 0.90 mM $CaCl_2$, 0.49 mM $MgCl_2$, 2.7 mM KCl, and 138 mM NaCl, pH 7.4)
16. Staining buffer: (DPBS with $Ca^{2+}$ and $Mg^{2+}$, containing 0.02% $NaN_3$ and 2% FBS)
17. 12×75 mL polystyrene tubes
18. Hydrodish HD24—24-well plate with integrated pH sensors Procedures 1. A Hydrodish HD24 plate was coated with 0.5 mL/well of anti-CD3 antibody (10 μg/mL in PBS) and incubated at RT for 6 hr
2. Cells from flasks containing activated CD8+ T cells (with Dynabeads; remove Dynabeads with magnet) were counted and adjusted cell density to $1\times10^6$ cells/mL in media
3. Lactic acid was prepared at 120 mM
4. HCl was prepared at 120 mM
5. Sodium lactate was prepared at 120 mM
6. L-DOS47 was prepared at 10 μg/mL
7. Urea was prepared at 20 and 40 mM
8. Buffer was removed from wells
9. 0.5 mL of CD8+ T cells, followed by 0.1 mL anti-CD28 Ab (15 μg/mL), 0.1 mL L-DOS47 and/or urea, 0.1 mL LA or HCl, and/or 0.1 mL sodium lactate solution was added to appropriate wells
10. Plates were incubated at 37° C. and 5% $CO_2$ for 2 days; pH change was monitored by placing the 24-well plate on the SDR inside the incubator
11. Samples were transferred from the 24-well plate to microfuge tubes, cells were spun down at 350×g for 5 min, and then the supernatants were removed and frozen for IL-2 and IFNγ ELISA assays.

Flow Cytometry Analysis

12. Cells were resuspended in 0.5 mL Staining buffer and 100 μL/well were transferred to a round-bottom 96-well plate for staining
13. Plate was centrifuged at 350 g for 4 min, supernatant was discarded with multi-channel pipette
14. 50 μL/well of the biotin-anti-PD-1 antibody (1:100 in Staining buffer), biotin-LDOS47 (1:80), biotin-urease (1:70), and isotype control (1:20) was added to corresponding wells
15. Mixed and incubated on ice for 30 min
16. Plate was washed 3× with 100 μL/well Staining buffer by centrifugation at 350 g for 4 min
17. 50 μL/well PE-Streptavidin (1:1500 in Staining buffer) was added and cells were resuspended well.
18. Plate was covered with tin foil and incubated on ice for 30 min
19. Plate was washed 3× as in step 16 above
20. Cells were fixed by resuspending cell pellet from the last wash in 50 μL/well of 1% paraformaldehyde in PBS
21. Plate was covered with tin foil and incubated at RT for 15 min
22. Buffer was removed from wells and cells were resuspended in 100 μL/well Staining buffer
23. Cells were mixed and plate was covered with tin foil and stored at 2-8° C.
24. Next day, 100 μL/well Staining buffer was added to each well
25. Cells were mixed and data was collected for each well using the Guava flow cytometer
26. Data was analyzed using FCS Express software ELISA to Determine IL-2 Concentration in Cell Supernatants Materials:

1. NaCl, EMD, SX0425-5 (FW 58.44)
2. KCl, EMD, PX1405-5 (FW 74.55)
3. $KH_2PO_4$, EMD 1565-5 (FW136.09)
4. $Na_2HPO_4$, Fisher Scientific S375-212 (FW141.96)
5. Tris BASE, Fisher Scientific, B154-1 (FW121.14)
6. Bovine Serum albumin (BSA), Roche REF10735086001
7. $H_2SO_4$, Fluka 17025 (FW98.07, d1.83, 96%, 17.9 M)
8. Human IL-2 DuoSet ELISA, R&D Systems, Cat # DY202:
   a. Human IL-2 Capture Antibody, Part #840104
   b. Human IL-2 Detection Antibody, Part #840105
   c. Human IL-2 standard, Part #840106
   d. Streptavidin-HRP, Part #893975
9. Substrate Solution A and B, R&D Systems, Catalog # DY999
10. ELISA plate, 96 well EIA/RIA Plate, Costar 3590
11. Substrate Solution A and B, R&D Systems, Catalog # DY999
12. TMB (3,3',5,5'-Tetramethylbenzidine, Aldrich, 860336-1G)
13. Dimethyl sulfoxide, Sigma, D8418-50 ml
14. Hydrogen Peroxide, 30%, Fisher H325-500
15. Sodium citrate tribasic, Sigma H325-500
16. Acetic acid glacial, BDH 3098-3.8LP
17. Plate reader, Molecular Device-2
18. Samples: Cell culture supernatants Buffers and Solutions:

1. PBS: 137 mM NaCl, 2.7 mM KCl, 8.1 mM $Na_2HPO_4$, 1.5 mM $KH_2PO_4$, pH 7.2-7.4, 0.2 μm filtered. Weigh 8.01 g NaCl, 0.201 g KCl, 1.15 g $Na_2HPO_4$, 0.204 g $KH_2PO_4$ in a 1 L beaker. Dissolve the salts in 950 ml water. Adjust the pH to 7.2-7.4. Transfer the buffer to a 1 L volumetric flask. Top to the 1 L marker. Filter through a 0.22 um disk filter.
2. Wash Buffer: 0.05% Tween® 20 in PBS, pH 7.2-7.4. Add 0.50 ml Tween 20 into 1 L PBS in a 1 L bottle, and flip the bottle until the surfactant is dissolved and mixed.
3. Block Buffer: 3% BSA in PBS, pH 7.2-7.4, 0.2 μm filtered. Dissolve 1.5 g BSA in 50.0 mL PBS. Store at 4° C.
4. Reagent Diluent: 0.1% BSA, 0.05% Tween 20 in PBS, 0.2 μm filtered. Dissolve 0.50 g BSA and 250 μl Tween 20 in 500 ml PBS. Mix well, and filter through with a 0.22 μm filter to a 0.5 L bottle. Store at 4° C.
5. Acetate-citrate buffer: weigh 2.1 g citric acid monohydrate, and dissolve in 500 ml water, add 0.625 ml glacial acetic acid. Adjust the pH to 4.5 using 5N NaOH.
6. TMB stock solution: Weigh 93.0 mg of TMB in 4 ml DMSO, store in dark (stable for 1 Month at RT)
7. Substrate Solution: Just before use, mix 8.0 ml Color Reagent A ($H_2O_2$) and 8.0 ml Color Reagent B (Tetramethylbenzidine) in a 50 ml screw-caped tube.
8. Stop Solution: 2 N $H_2SO_4$. Dilute 5.6 ml $H_2SO_4$ (36N) to 100 ml water.

9. Human IL-2 standard stock solution (60 ng/mL). Add 0.500 ml Regent diluent to the vial of the IL-2 vial. Close the cap and gently flip over the vial to dissolve the protein. Store at 4° C.
10. Mouse Anti-Human IL-2 Capture Antibody stock solution (480 µg/mL): Reconstitute each vial with 0.5 mL of PBS. Store at 4° C.
11. Biotinylated Goat Anti-Human IL-2 Detection Antibody stock (6.0 µg/mL): Reconstitute each vial with 1.0 mL of Reagent Diluent. Close the cap and gently flip over the vial to dissolve the protein. Store at 4° C.

Procedures:
1. Preparation of the capture antibody working solution (4 µg/ml): Into 16.0 ml PBS in a 50 ml screw-capped tube, 0.133 ml of Mouse Anti-Human IL-2 Capture Antibody stock solution (480 µg/ml) was added and vortexed to mix.
2. The plate was coated by adding 100 µl/well capture antibody working solution. The plate was covered with plastic film and incubated overnight at 4° C.
3. The next morning, each well was aspirated and washed by filling each well with 300 µl Wash Buffer and completely removing liquid. The process was repeated two times for a total of three washes. After the last wash, any remaining Wash Buffer was removed by aspirating.
4. Plates were blocked by adding 200 µL/well of Block Buffer to each well. Plates were incubated at room temperature for 2 hours with gentle shaking (~100 rpm)
5. The aspiration/wash steps were repeated as in step 3. The plates were then ready for sample addition.
6. During blocking, the IL-2 working standard solution was prepared for a 7-point standard curve by a 2-fold serial dilution into the Reagent Diluent with the first standard concentration of 1000 pg/ml in a 1.0 ml Eppendorf tube. To make the 1000 µg/ml standard, 16.7 µL 60 ng/mL standard was diluted to 1.50 mL Reagent diluent buffer and vortexed.
7. Each sample was diluted 20-fold by mixing 25 uL of supernatant with 475 µL of reagent diluent.
8. After the wash in Step 5, 100.0 ul/well of each standard and sample working solution was pipetted to the wells according to the plate layout
9. The plate was covered with plastic film, and incubated at RT for 1.5 hours with gentle shaking (~100 rpm)
10. The aspiration/wash was repeated as in step 3.
11. Preparation of the detection antibody working solution (100 ng/ml): Into 16.0 ml Reagent Diluent in a 50 ml screw-capped tube, 0.266 ml of Biotinylated Goat Anti-Human IL-2 Detection Antibody stock solution, and 320 µl normal goat serum was added and vortexed to mix.
12. 100 µL/well of the Detection Antibody working solution was added; the plate was covered with plastic film. The plate was incubated at RT for 1.5 hours with gentle shaking (~100 rpm)
13. The aspiration/wash as in step 3 was repeated.
14. Preparation of the Streptavidin-HRP working solution. 40× dilution: Into 16.0 ml Reagent Diluent in a 50 ml screw-capped tube, 0.400 ml of Streptavidin-HRP stock solution was added and vortexed to mix.
15. 100 µL of the working dilution of Streptavidin-HRP was added to each well. The plate was covered and incubated for 20 minutes at room temperature with gentle shaking (~100 rpm).
16. The aspiration/wash as in step 3 was repeated.
17. 100 µL of Substrate Solution was added to each well. The plate was incubated for 30 minutes at room temperature with shaking (~200 rpm). The time depends on color developed, usually between 10 to 60 min. The OD was checked before adding Stop solution. Placing the plate in direct light was avoided.
18. 100 µL of Stop Solution was added to each well. The plate was gently tapped to ensure thorough mixing.
19. The optical density of each well was determined immediately, using a microplate reader set to 450 nm for signal OD and to 570 nm for background OD. Readings at 570 nm were subtracted from the readings at 450 nm to correct for optical imperfections in the plate
20. The best fit for the standard curve was determined and the equation was used to interpolate the IL-2 concentration for each sample.

ELISA to determine IFNγ concentration in cell supernatants
1. Instrument and Materials:
 1.1. Plate reader: Spectra Max M2, Molecular Devices
 1.2. NaCl, EMD, SX0425-5 (FW 58.44)
 1.3. KCl, EMD, PX1405-5 (FW 74.55)
 1.4. KH2PO4, EMD 1565-5 (FW136.09)
 1.5. Na2HPO4, Fisher Scientific S375-212 (FW141.96)
 1.6. Tris BASE, Fisher Scientific, BP154-1 (FW121.14)
 1.7. Bovine Serum albumin (BSA), Roche REF10735086001
 1.8. H2SO4, Fluka 17025 (FW98.07, d1.83, 96%, 17.9 M)
 1.9. Normal goat serum, Sigma, G9023-10 ml
 1.10. Human IFN-gamma DuoSet ELISA, R&D Systems, Cat # DY285:
  1.10.1. Human IFN-γ Capture Antibody, 240 µg/vial, Part #840101, working concentration 4.00 µg/ml
  1.10.2. Human IFN-γ Detection Antibody, 12.0 µg/vial, Part #840102, working concentration 200 ng/ml
  1.10.3. Human IFN-γ standard, 32.5 ng/vial, Part #840103
  1.10.4. Streptavidin-HRP, Part #893975, working concentration 40-fold dilution
 1.11. Substrate Solution A and B, R&D Systems, Catalog # DY999
 1.12. TMB (3,3',5,5'-Tetramethylbenzidine, Aldrich, 860336-1G)
 1.13. Dimethyl sulfoxide, Sigma, D8418-50 ml
 1.14. Hydrogen Peroxide, 30%, Fisher H325-500
 1.15. Sodium citrate tribasic, Sigma H325-500
 1.16. Acetic acid glacial, BDH 3098-3.8LP
 1.17. ELISA plate, 96 well EIA/RIA Plate, Costar 3590
 1.18. Samples: Cell culture supernatants
2. Buffers and Solutions:
 2.1. PBS: 137 mM NaCl, 2.7 mM KCl, 8.1 mM $Na_2HPO_4$, 1.5 mM $KH_2PO_4$, pH 7.2-7.4, 0.2 µm filtered. Weigh 8.01 g NaCl, 0.201 g KCl, 1.15 g $Na_2HPO_4$, 0.204 g $KH_2PO_4$ in a 1 L beaker. Dissolve the salts in 950 ml water. Adjust the pH to 7.2-7.4. Transfer the buffer to a 1 L volumetric flask. Top to the 1 L marker. Filter through a 0.22 um disk filter.
 2.2. Wash Buffer: 0.05% Tween® 20 in PBS, pH 7.2-7.4. Add 0.50 ml Tween 20 into 1 L PBS in a 1 L bottle, and flip the bottle until the surfactant is dissolved and mixed
 2.3. Block Buffer: 3% BSA in PBS, pH 7.2-7.4, 0.2 µm filtered. Dissolve 1.50 g BSA in 50.0 mL PBS. Filter with 0.22 µm filter, and store at 4° C.

2.4. Reagent Diluent: 0.1% BSA, 0.05% Tween 20 in PBS, 0.2 μm filtered. Dissolve 0.50 g BSA and 250.0 μl Tween 20 in 500 ml PBS. Mix well, and filter through with a 0.22 μm filter to a 0.5 L bottle. Store at 4° C.

2.5. Acetate-citrate buffer: weigh 2.1 g citric acid monohydrate, and dissolve in 500 ml water, add 0.625 ml glacial acetic acid. Adjust the pH to 4.5 using 5N NaOH.

2.6. TMB stock solution: Weigh 58.0 mg of TMB in 5 ml DMSO, store in dark (stable for 1 Month at RT)

2.7. Substrate Solution: Just before use, mix 8.0 ml Color Reagent A ($H_2O_2$) and 8.0 ml Color Reagent B (Tetramethylbenzidine) in a 50 ml screw-caped tube.

2.8. Stop Solution: 2 N $H_2SO_4$. Dilute 5.6 ml $H_2SO_4$ (36N) to 100 ml water 2.9. Human IFN-γ standard stock solution (60 ng/ml). Add 0.500 ml Regent diluent to the vial of the INF-γ. Close the cap and gently flip over the vial to dissolve the protein. Store at 4° C.

2.10. Mouse Anti-Human IFN-γ Capture Antibody stock solution (480 μg/ml): Reconstitute each vial with 0.5 mL of PBS. Make 6 aliquots, 83.3 μl/each in 0.6 ml micro-centrifugal tube. Store at 4° C.

2.11. Biotinylated Goat Anti-Human IFN-γ Detection Antibody stock (12.0 μg/ml): Reconstitute each vial with 1.0 mL of Reagent Diluent. Close the cap and gently flip over the vial to dissolve the protein. Make 6 aliquots, 166.0 μl/each in 0.6 ml micro-centrifugal tube. Store at 4° C.

3. Procedures 3.1. Preparation of the capture antibody working solution (4.00 μg/ml): Into 16.0 ml PBS in a 50 ml screw-capped tube, 133.0 μl of Mouse Anti-Human IFN-γ Capture Antibody stock solution (480 μg/ml) was added and vortex to mix (used within 20 minutes).

3.2. 2 plates were coated by adding 100 μl/well capture antibody working solution. The plate was covered with plastic film and incubated overnight at 4° C.

3.3. The next morning, each well was aspirated completely and washed by filling each well with 300 μl Wash Buffer. The process was repeated two times for a total of three washes. After the last wash, any remaining Wash Buffer was removed by aspirating.

3.4. Plates were blocked by adding 200 μL/well of Block Buffer to each well. Plates were incubated at room temperature for 2 hours with gentle shaking (~100 rpm)

3.5. The aspiration/wash was repeated as in step 3.3. The plates were then ready for sample addition.

3.6. During blocking, the IFN-γ working standard solution was prepared for a 7-point standard curve by a 2-fold serial dilution into the Reagent Diluent with the first standard concentration of 1000 pg/ml in a 1.5 ml Eppendorf tube.

3.7. Each sample was diluted 20-fold by mixing 25 ul of supernatant with 475 uL of reagent diluent.

3.8. After the wash in Step 3.5, 100.0 ul/well of each standard and sample working solution was pipetted to the wells according to the plate layout.

3.9. The plate was covered with plastic film, and incubated at RT for 1.5 hours with gentle shaking (~100 rpm)

3.10. The aspiration/wash were repeated as in step 3.3.

3.11. Preparation of the detection antibody working solution (200 ng/ml): Into 16.0 ml Reagent Diluent in a 50 ml screw-capped tube, 0.266 ml of Biotinylated Goat Anti-Human IFN-γ Detection Antibody stock solution, and 160 μl goat serum were added and vortexed to mix. Plates were incubated at RT for at least 1 hour before use.

3.12. 100 μL/well of the Detection Antibody working solution was added; the plate was covered with plastic film. The plate was incubated at RT for 1.5 hours with gentle shaking (~100 rpm)

3.13. The aspiration/wash as in step 3.3 was repeated.

3.14. 100 μL of the working dilution of Streptavidin-HRP was added to each well. The plate was covered and incubated for 20 minutes at room temperature with gentle shaking (~100 rpm). Placing the plate in direct light was avoided.

3.15. The aspiration/wash as in step 3.3 was repeated.

3.16. Preparation of substrate working solution: 9.0 ml acetate-citrate (100 mM, pH 5.0) buffer, 1.0 ml DMSO, and 0.25 mL TMB (58 mg in 5.0 ml DMSO), and 20.0 μl $H_2O_2$ (30%) were mixed 3.17. 100 μL of Substrate Solution was added to each well and incubated for 20 minutes at room temperature with shaking (~200 rpm). The time depends on color developed, usually between 10 to 60 min. The OD was checked before adding Stop solution. Placing the plate in direct light was avoided.

3.18. 100 μL of Stop Solution was added to each well. The plate was gently tapped to ensure thorough mixing.

3.19. The optical density of each well was determined immediately, using a microplate reader set to 450 nm for signal OD and to 570 nm for background OD. Readings at 570 nm were subtracted from the readings at 450 nm to correct for optical imperfections in the plate 3.20. The best fit for the standard curve was determined and the equation was used to interpolate the IFNγ concentration for each sample.

As has been shown herein, an acidic microenvironment has several immuno-inhibitory effects on activated Jurkat cells, including the inhibition of T cell proliferation, IL-2 production, and expression of PD-1 at the cell surface.

Addition of L-DOS47 and urea to the media raises the extracellular pH, and also partially restores levels of Jurkat cell proliferation, IL-2 production, and surface expression of PD-1.

Tumor cells pre-treated with IFNγ also inhibit production of IL-2 from activated Jurkat cells.

Treatment of MDA-MB-231 breast cancer cells with lactic acid reduces the pH of the media and increases PD-L1 expression. Treatment with L-DOS47+ urea reduces PD-L1 expression to levels observed on untreated cells.

PD-L1 levels are unchanged on similarly treated SKOV-3 ovarian cancer cells.

Activated primary CD8+ T cells express PD-1 and secrete IL-2 and IFNγ. Incubation with lactic acid increases PD-1 expression, has little effect on IL-2 production, and significantly impairs IFNγ production.

Treatment of lactic acid-cultured CD8+ T cells with L-DOS47+ urea increases IL-2 production, lowers PD-1 expression and restores IFNγ production to levels observed on untreated activated cells.

L-DOS47 treatment represents a novel method to reduce acid-induced immunosuppressive PD-1/PD-L1 interactions, by lowering expression of PD-1 and PD-L1 on T cells and tumor cells, respectively.

The above disclosure generally describes the present invention. Although specific terms have been employed herein, such terms are intended in a descriptive sense and not for purposes of limitation.

All publications, patents and patent applications cited above are herein incorporated by reference in their entirety to the same extent as if each individual publication, patent or patent application was specifically and individually indicated to be incorporated by reference in its entirety.

Although preferred embodiments of the invention have been described herein in detail, it will be understood by those skilled in the art that variations may be made thereto without departing from the spirit of the invention or the scope of the appended claims.

What is claimed is:

1. A method for restoring function to acidified T cells, the method comprising administering urease to the T cells, wherein the urease is conjugated to an antibody specific for CEACAM6.

2. The method of claim 1, wherein restoring function comprises increasing production of cytokines.

3. The method of claim 2, wherein the cytokines comprise IL-2.

4. The method of claim 1, wherein the T cells are acidified relative to physiological pH such that the T cells are in an environment of a pH of less than about 7.2, less than about 7.1, less than about 7.0, less than about 6.9, or less than about 6.8.

5. The method of claim 4, wherein the T cells are acidified with lactate produced by a solid tumor.

6. The method of claim 1, wherein the T cells are in the presence of urea, either native or administered.

7. The method of claim 1, wherein the T cells express PD-1, optionally at higher than normal levels compared to a non-acidified T cell and wherein the urease inhibits PD-1 expression and/or activation.

8. The method of claim 1, wherein the antibody is an AFAIKL2 antibody or a 2A3 antibody.

9. The method of claim 1, wherein the urease inhibits PD-L1 expression on acid sensitive cancer cells.

10. The method of claim 1, further comprising administering to said acidified T cells an active agent selected from a PD-1 inhibitor, a chemotherapeutic agent, radiation, a hormone, a cytokine and combinations thereof.

11. The method of claim 10, wherein the cytokine is IL-2.

12. The method of claim 1, in conjunction with immunotherapy.

13. The method of claim 12, wherein the immunotherapy is adoptive T cell therapy.

14. The method of claim 1, wherein the urease is administered in an amount sufficient to increase the pH in the vicinity of the acidified T cells to physiological levels.

15. The method of claim 14, wherein the urease is administered in an amount sufficient to decrease PD-1 expression on the T cells.

16. The method of claim 14, wherein the pH is increased to 7.2.

17. The method of claim 1, wherein the urease is administered in an amount that does not cause significant T cell death or harm.

18. A method of normalizing IL-2 production by T cells subjected to acidified conditions, the method comprising administering urease to the T cells, wherein the urease is conjugated to an antibody specific for CEACAM6.

19. A method of inhibiting lactate-induced T cell tolerance to tumor cells, the method comprising administering urease to the T cells, wherein the urease is conjugated to an antibody specific for CEACAM6.

20. A method for increasing an immune response to a CEACAM6+ and/or PD-L1+ cancer by reactivating acidified T cells, the method comprising administering urease to a subject having a CEACAM6+ and/or PD-L1+ cancer, wherein the urease is conjugated to an antibody specific for CEACAM6.

21. The method of claim 20, wherein said urease increases T cell infiltration into said cancer, said cancer being a solid tumor.

22. A composition comprising or consisting of urease conjugated to an antibody specific for CEACAM6 and a PD-1 inhibitor and/or a PDL-1 inhibitor for restoring T cell function.

23. The composition of claim 22, wherein said composition increases IL-2 production by T cells.

* * * * *